US006214274B1

(12) United States Patent
Melius et al.

(10) Patent No.: US 6,214,274 B1
(45) Date of Patent: Apr. 10, 2001

(54) PROCESS FOR COMPRESSING A WEB WHICH CONTAINS SUPERABSORBENT MATERIAL

(75) Inventors: Shannon Kathleen Melius, Appleton; David Arthur Fell, Neenah; William Grover Reeves, Appleton; Donald Joseph Sanders, Larsen; Heath David Van Wychen, Kimberly; Michael Barth Venturino, Appleton; Palani Raj Ramaswami Wallajapet, Wauwatosa, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/334,186

(22) Filed: Jun. 16, 1999

(51) Int. Cl.⁷ .................................................. B29C 53/18
(52) U.S. Cl. ............................................................ 264/280
(58) Field of Search ............................................. 264/280

(56) References Cited

U.S. PATENT DOCUMENTS

| | | |
|---|---|---|
| 3,881,490 | 5/1975 | Whitehead et al. . |
| 3,901,236 | 8/1975 | Assarsson et al. . |

(List continued on next page.)

FOREIGN PATENT DOCUMENTS

| | | |
|---|---|---|
| 681755 | 7/1995 | (AU) . |
| 217 032 A2 | 4/1987 | (EP) . |
| 359 615 A1 | 3/1990 | (EP) . |
| 437 816 B1 | 7/1995 | (EP) . |
| 690 077 A1 | 1/1996 | (EP) . |
| WO 93/21879 A1 | 11/1993 | (WO) . |
| WO 96/32084 A1 | 10/1996 | (WO) . |
| WO 98/24392 A1 | 6/1998 | (WO) . |
| WO 98/24621 A1 | 6/1998 | (WO) . |
| WO 98/24960 A1 | 6/1998 | (WO) . |
| WO 98/27276 A1 | 6/1998 | (WO) . |
| WO 98/51251 A1 | 11/1998 | (WO) . |

OTHER PUBLICATIONS

Billmeyer, Jr., Fred W., "Textbook of Polymer Science, Third Edition", p. 7 (Undated).
Buchholz, Fredric L./Graham, Andrew T., Wiley–VCH, "Modern Superabsorbent Polymer Technology", 1998, pp. 45 and 140–143.
"Acrylic Ester Polymers," *Kirk–Othmer Encyclopedia of Chemical Technology,* Fourth Edition, vol. 1, John Wiley & Sons Publishers, 1991, pp. 315–317.

(List continued on next page.)

*Primary Examiner*—Leo B. Tentoni
(74) *Attorney, Agent, or Firm*—Paul Yee

(57) ABSTRACT

A process and apparatus for compacting a web (12) which contains a superabsorbent material (32) can include a plasticizing of the superabsorbent material contained in the web (12), and a compressing of the web (12) at a relatively low pressure. The selected, low pressure can be arranged to substantially avoid an excessive fracturing of the superabsorbent material.

43 Claims, 23 Drawing Sheets

U.S. PATENT DOCUMENTS

| | | |
|---|---|---|
| 3,902,230 | 9/1975 | Schwarz . |
| 4,076,663 | 2/1978 | Masuda et al. . |
| 4,117,184 | 9/1978 | Erickson et al. . |
| 4,223,059 | 9/1980 | Schwarz . |
| 4,260,443 | 4/1981 | Lindsay et al. . |
| 4,285,100 | 8/1981 | Schwarz . |
| 4,286,082 | 8/1981 | Tsubakimoto et al. . |
| 4,326,527 * | 4/1982 | Wollangk et al. .................... 604/371 |
| 4,347,092 | 8/1982 | Hlaban et al. . |
| 4,354,901 | 10/1982 | Kopolow . |
| 4,500,316 | 2/1985 | Damico . |
| 4,552,618 | 11/1985 | Kopolow . |
| 4,573,988 | 3/1986 | Pieniak et al. . |
| 4,600,458 | 7/1986 | Kramer et al. . |
| 4,605,402 | 8/1986 | Iskra . |
| 4,610,678 | 9/1986 | Weisman et al. . |
| 4,646,362 | 3/1987 | Heran et al. . |
| 4,663,220 | 5/1987 | Wisneski et al. . |
| 4,685,914 | 8/1987 | Holtman . |
| 4,699,823 | 10/1987 | Kellenberger et al. . |
| 4,701,177 | 10/1987 | Ellis et al. . |
| 4,704,116 | 11/1987 | Enloe . |
| 4,753,646 | 6/1988 | Enloe . |
| 4,851,069 | 7/1989 | Packard et al. . |
| 4,886,512 | 12/1989 | Damico et al. . |
| 4,916,005 | 4/1990 | Lippert et al. . |
| 4,921,543 | 5/1990 | Omran et al. . |
| 4,921,643 | 5/1990 | Walton et al. . |
| 4,938,753 | 7/1990 | Van Gompel et al. . |
| 4,940,464 | 7/1990 | Van Gompel et al. . |
| 4,986,882 | 1/1991 | Mackey et al. . |
| 5,019,073 | 5/1991 | Roessler et al. . |
| 5,049,235 | 9/1991 | Barcus et al. . |
| 5,102,501 | 4/1992 | Eber et al. . |
| 5,226,992 | 7/1993 | Morman . |
| 5,252,275 | 10/1993 | Sultze et al. . |
| 5,324,575 | 6/1994 | Sultze et al. . |
| 5,399,219 | 3/1995 | Roessler et al. . |
| 5,401,267 | 3/1995 | Couture-Dorschner . |
| 5,411,497 | 5/1995 | Tanzer et al. . |
| 5,425,725 | 6/1995 | Tanzer et al. . |
| 5,433,715 | 7/1995 | Tanzer et al. . |
| 5,486,166 | 1/1996 | Bishop et al. . |
| 5,490,846 | 2/1996 | Ellis et al. . |
| 5,509,915 | 4/1996 | Hanson et al. . |
| 5,540,796 | 7/1996 | Fries . |
| 5,558,659 | 9/1996 | Sherrod et al. . |
| 5,562,645 | 10/1996 | Tanzer et al. . |
| 5,562,650 | 10/1996 | Everett et al. . |
| 5,593,399 | 1/1997 | Tanzer et al. . |
| 5,595,618 | 1/1997 | Fries et al. . |
| 5,601,542 | 2/1997 | Melius et al. . |
| 5,605,735 | 2/1997 | Zehner et al. . |
| 5,607,550 | 3/1997 | Akers . |
| 5,624,429 | 4/1997 | Long et al. . |
| 5,651,862 | 7/1997 | Anderson et al. . |
| 5,669,901 | 9/1997 | LaFortune et al. . |
| 5,820,973 | 10/1998 | Dodge, II et al. . |
| 5,858,515 | 1/1999 | Stokes et al. . |
| 5,904,675 | 5/1999 | Laux et al. . |
| 5,948,829 | 9/1999 | Wallajapet et al. . |
| 5,985,434 | 11/1999 | Qin et al. . |
| 6,007,528 | 12/1999 | Osborn, III . |
| B1 4,315,508 | 11/1988 | Bolick . |
| B1 5,147,343 | 3/1998 | Kellenberger . |

OTHER PUBLICATIONS

Fellers, Christer, "Edgewise Compression Strength of Paper," *Handbook of Physical and Mechanical Testing of Paper and Paperboard,* vol. 1, 1983, pp. 349–381.

American Society for Testing Materials (ASTM) Designation: D 4032–82, "Standard Test Method for Stiffness of Fabric by the Circular Bend Procedure," pp. 702–706, published Aug. 1982.

Federal Test Method Standard (FTMS) No. 191A, Method 5514, "Water Resistance of Cloth; Low Range, Hydrostatic Pressure Method," Jul. 20, 1978, 3 pages.

TAPPI Official Test Method T 543 om–94, "Bending Resistance of Paper (Gurley Type Tester)," published by the TAPPI Press, Atlanta, Georgia, pp. 1–7 (Undated).

* cited by examiner

PROCESS FOR COMPRESSING A WEB WHICH CONTAINS SUPERABSORBENT MATERIAL

FIELD OF THE INVENTION

The present invention relates to a process for densifying an absorbent web. More particularly, the present invention relates to a process for densifying a web which contains superabsorbent material. The densified web can advantageously exhibit desired levels of strength, softness and flexibility.

BACKGROUND OF THE INVENTION

The performance objectives of disposable absorbent articles, such as infant diapers, include leakage prevention, dry feel to the wearer, and a comfortable fit throughout the product life. Accordingly, absorbent articles have typically contained an absorbent core to provide liquid handling and other absorbent functionalities required to meet the product performance objectives. The absorbent core of a conventional absorbent article has typically been composed of absorbent fibers, and a superabsorbent material has typically been combined with the absorbent fibers to increase the liquid absorbent capacity. The absorbent core has been formed in a substantially rectangular shape. The absorbent core has also been formed in an hourglass shape, a I-shape, a T-shape, or similar configuration with a reduced absorbent width in the central crotch region for improved fit and comfort.

Conventional absorbent cores have incorporated dry-formed materials which have been produced with various conventional airlaying techniques. The airlaying techniques have typically laid an air-directed mixture of absorbent fibers and superabsorbent to form a web of the absorbent material. When dry, the conventional dry-formed absorbent structures have been soft and conformable, but have had low strength. In addition, the dry-formed structures have had low integrity after they have been wetted.

Conventional absorbent cores have also incorporated wet-formed materials which have been produced with various wet-laying techniques. The wet-laying techniques have typically formed an absorbent web produced from a precursor material composed of a mixture of fibers and superabsorbent particles combined with water or other aqueous liquid. A particular wet-laying technique has processed the precursor material into a foam, and the foam has then been employed to form the desired web of absorbent material. The absorbent structures produced from wet-formed absorbent materials have had greater strength and greater integrity. In particular, the wet-formed absorbent structures have exhibited greater strength and greater integrity after the absorbent materials have absorbed liquid. The wet-formed absorbent materials, however, have also had excessive stiffness and rigidity, particularly when the absorbent materials have been provided at the basis weights and amounts needed to provide desired levels of total absorbent capacity.

Particular methods for reducing the stiffness of absorbent web materials have included a passing of the material through the nip of a pair of counter-rotating compression rollers. Other methods have embossed the webs to impart increased flexibility. Still other methods have included a passing of the material through the nip of a pair of counter-rotating rollers having textured outer surfaces. The textured surfaces have been configured to produce localized stresses and localized strains which have helped to reduce the rigidity of the material. Where the webs contain superabsorbent particles, the compression rollers have been configured to fracture or crush the superabsorbent materials.

Conventional techniques, such as those mentioned above, have not been adequate for softening or compressing webs which contain superabsorbent materials. The conventional techniques have caused excessive fracturing of the superabsorbents and have increased the relative proportions of smaller superabsorbent particles in the webs. This change in the size distributions of the superabsorbent particles has adversely affected the absorbent properties of the web, has increased the tendency of the superabsorbent to shake-out of the web, and has allowed the generation of excessive dust. In addition, the fracturing of the superabsorbent material has adversely affected various absorbent properties, such as the intake rate of the superabsorbent and the ability of the superabsorbent to swell under pressure.

As a result, there remains a need for improved methods for compressing or otherwise processing stiff absorbent materials to improve the strength, softness, flexibility, wet integrity and absorbent capacity of the materials.

BRIEF DESCRIPTION OF THE INVENTION

Generally stated, the present invention can provide a process for compacting and/or densifying a web which contains a superabsorbent material. In particular aspects, the process includes a compressing of a web which includes a plasticized superabsorbent material. In further aspects, the web can be compressed at a relatively low pressure which can be selected to substantially avoid an excessive damaging of the superabsorbent material.

In its various aspects, the present invention can more effectively and efficiently compact and/or density a web which contains particles of superabsorbent material. In particular, the compacting or densifying process of the invention can advantageously maintain the desired sizes, shapes, physical properties and absorbent properties of the superabsorbent material in the final, compressed web. When articles incorporate the absorbent structures that are produced in accordance with the present invention, the articles can exhibit increased strength, improved fit, reduced leakage, and reduced clumping, bunching or sagging during use.

BRIEF DESCRIPTION OF THE DRAWINGS

The present invention will be more fully understood and further advantages will become apparent when reference is made to the following detailed description of the invention and the drawings, in which.

DETAILED DESCRIPTION OF THE INVENTION

Figure 1:
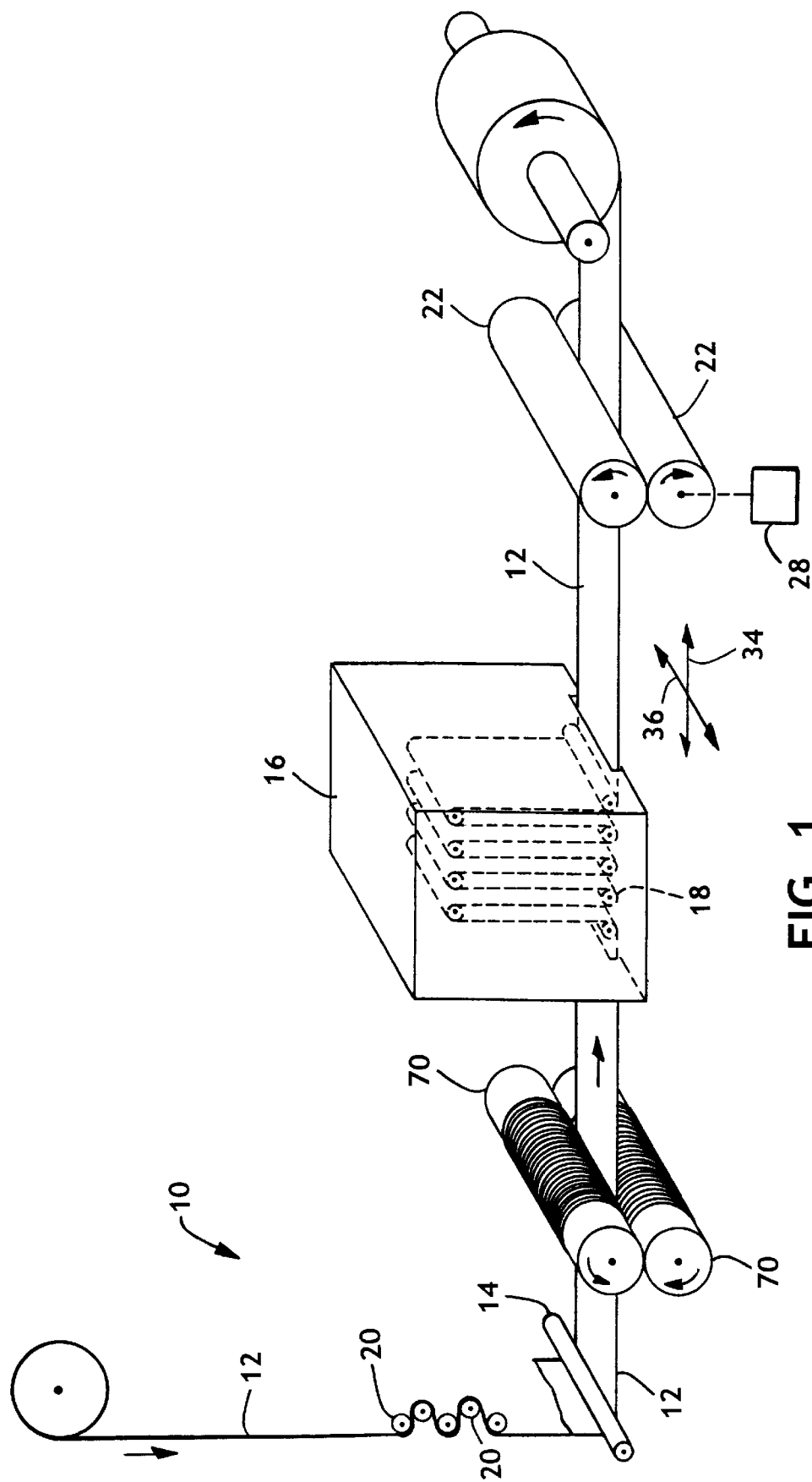
FIG. 1 representatively shows a schematic view of an apparatus and method of the present invention.

The present invention provides distinctive methods for densifying and/or softening superabsorbent-containing materials, such as composites composed of a mixture of fibers and particles of superabsorbent material (SAM), or a composite composed of superabsorbent particles and a foamed matrix material. The superabsorbent material may have a substantially homogeneous distribution, a layered or stratified distribution or a gradient distribution through the composite. The superabsorbent-containing materials can then be employed to form absorbent structures in personal care products, such as diapers, feminine care products, children's training pants, adult incontinence products and the like.

Examples of absorbent structures that may include a softening and/or compressing prior to incorporation into a product can include, but are not limited to, superabsorbent-containing wetlaid structures, superabsorbent-containing dry-laid structures, superabsorbent-containing foamed structures, superabsorbent-containing air-laid structures, and the like, as well as combinations thereof. Wet-formed webs or structures can, for example, be produced by employing a water-containing mixture of superabsorbent material and fibrous material. Wet-formed structures or webs can also be produced by employing a water-containing mixture of superabsorbent material and fibrous material, wherein the mixture has been provided in the configuration of a foam. Dry-formed webs or structures can, for example, be produced by employing an air-suspension or air-entrained mixture of fibrous material and superabsorbent material.

Examples of suitable wetlaid, superabsorbent structures can include those produced by the method described in U.S. Pat. No. 5,651,862 entitled WET-FORMED ABSORBENT COMPOSITE by R. Anderson et al., which issued Jul. 29, 1997. Examples of airlaid, superabsorbent structures are described in U.S. Pat. No. 5,509,915 entitled THIN ABSORBENT ARTICLE HAVING RAPID UPTAKE OF LIQUID by W. Hanson et al. which issued Apr. 23, 1996. The entire disclosure of these documents are incorporated herein by reference in a manner that is consistent herewith.

The techniques of the present invention can compact and/or densify an absorbent structure without excessively damaging the superabsorbent material in the structure, or excessively degrading the functional properties of the absorbent structure. The techniques of the invention can help soften the absorbent material and enhance the performance of its resulting absorbent structure.

The technique of the invention can be further improved by appropriately choosing the constituent materials in the absorbent web structure. For example, adding crosslinked cellulose fibers to the absorbent structure can impart bulk and softness. Increasing the amount of superabsorbent can also impart softness due to reduced fiber-to-fiber bonding.

It should also be noted that, when employed in the present disclosure, the terms "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof.

With reference to FIGS. 1, 2, 3 and 4, the invention can provide a distinctive process and apparatus for compacting and/or densifying a web 12 which contains a superabsorbent material 32. Generally stated, the process includes a compressing of the web 12 while the web includes superabsorbent material which has been plasticized.

In desired arrangements, the invention can include a plasticizing of the superabsorbent material contained in the web 12, and a subsequent compaction or compression of the web 12. The compressing of the absorbent web 12 may be conducted at a selected, relatively low pressure, and the low pressure can be arranged to substantially avoid an excessive fracturing (e.g. cracking or breaking) or other damaging of the desired properties of the superabsorbent material 32. Additionally, the web can be compressed while being subjected to a selected compressing temperature. In particular aspects, a glass transition temperature (Tg) of the superabsorbent material has been, at least temporarily, adjusted, and the adjusted glass transition temperature is approximate to the selected compressing temperature. In a further aspect of the invention, the temperature of the superabsorbent can be raised to within a selected range or proportion of the glass transition temperature of the superabsorbent material.

The glass transition temperature of the superabsorbent material is a conventional parameter that is recognized in the art. Generally stated, the glass transition temperature (Tg) is a temperature where a material, such as a polymeric material, undergoes a marked change in properties associated with the virtual cessation of local molecular motion. Below its Tg, an amorphous material can have many of the properties associated with ordinary inorganic glasses, including the properties of hardness, brittleness, stiffness and transparency. For example, see the *Textbook of Polymer Science*, Billmeyer, (1984, Wiley) ISBN 0-471-03196-8, e.g. page 7. The glass transition temperature can reflect the mechanical properties of the material over a specified temperature range. Below Tg, a polymer is stiff, hard, brittle, and grasslike; above Tg, if the molecular weight is high enough, the polymer is relatively soft, limp, stretchable, and can be somewhat elastic. At even higher temperatures the material can flow and be tacky. Below the transition temperature, the majority of the polymer chains have a relatively fixed configuration, and little translation or rotation of polymer chains takes place. Above the glass-transition temperature, the polymer chain has sufficient thermal energy for rotational motion or considerable torsional oscillation; thus the glass-transition temperature marks the onset of segmental mobility. The glass transition is not sharp and takes place over a temperature range of several degrees. Accordingly, the Tg is taken as the midpoint of the temperature interval over which the discontinuity in properties occurs. Conventional techniques for determining Tg have, for example, employed a differential scanning calorimeter (DSC). See the *Kirk-Othmer Encycloredia of Chemical Technology*, 4th edition, Vol. 1, e.g. pp.315–317; and *Modern Superabsorbent Polymer Technology*, editors F. L. Bucholz and A. T. Graham, Wiley-VCH (1998), e.g. pp. 45 and 140–143.

The glass transition temperature of the superabsorbent material can, for example, be adjusted by subjecting the web 12 to a selected humidification. In desired aspects, the humidification can selectively raise the water content of the associated superabsorbent material. The humidification may also be employed to expose and adjust the web components to the desired compressing temperature. Desirably, the humidification can occur prior to the compressing and densification of the absorbent web 12. In particular aspects of the invention, particles of the superabsorbent material may become flattened, tend to form platelets or otherwise tend to retain a deformed shape when compressed. In additional aspects, the deformed superabsorbent particles can be configured to substantially overcome or otherwise relinquish their deformation when the superabsorbents are wetted. When subjected to the ordinary pressures that are encountered during normal use, the superabsorbent materials can be configured to expand and swell to return to approximately their original, undeformed shapes during the absorption of liquid. As a result, the superabsorbent material can advantageously retain or reacquire an ability to open up the matrix structure of the composite as the superabsorbent material swells.

In particular aspects, the superabsorbent material 32 can initially be provided in the web at a selected first moisture level. For example, the superabsorbent material can be provided for inclusion in the web 12 while the superabsorbent material contains the first moisture level. In other aspects, the superabsorbent material can be dried or otherwise conditioned to attain the first moisture level. Optionally, the superabsorbent and web can be both dried or otherwise conditioned to attain the desired first moisture level in the superabsorbent material. The superabsorbent and web can desirably be conditioned while combined together. In further aspects, the process can include a providing of a fibrous material or other matrix material for inclusion in the web. In the various configurations of the invention, the web 12 can be initially provided while the superabsorbent material contains the first moisture level, and the compressing of the web can be subsequently conducted while the superabsorbent material contains a second moisture level which is greater than the first moisture level.

Still other aspects of the invention can include heated calender rolls which can help to reduce the amount of pressure required to densify the absorbent web 12. Additionally, the humidification and calendering of the web 12 can be conducted in a combined operation to provide further advantages.

Additional softening procedures can be performed on the web either prior to, after, or instead of the calendering of the web 12. Such additional procedures may, for example, include embossing, compressing, compressing between matched grooved rolls, micro-straining and the like, as well as combinations thereof. The softening the web 12 in such a manner may provide the further advantage of breaking some of the bonds which would otherwise limit the swelling of the superabsorbent material in the web, thereby providing enhanced capacity to the structure. It is contemplated that the web 12 may be heated during the additional softening procedures.

In desired arrangements, the technique of the invention can include a selected flexing of the web 12. Where a softening flexation and a densification of the web are both employed, the absorbent web material 12 is desirably softened by the flexing prior to calendering. This configuration of the invention can be particularly advantageous for processing structures that are densified to thicknesses which approach the size of the superabsorbent particles in the web.

The various aspects of the present invention can be incorporated individually or in any desired combination, and can help to more effectively and efficiently unstiffen and soften a web which contains particles of superabsorbent material. In particular, the various aspects of the technique of the invention can advantageously maintain the desired shapes, physical properties and/or absorbent properties of the superabsorbent material. Additionally, the present invention can produce an absorbent article which provides improved fit, more softness and flexibility, better containment of the superabsorbent in the web, improved absorbency and reduced leakage.

With reference to FIG. 1, the process and apparatus of the invention can have an appointed machine-direction 34 and an appointed cross-direction 36. For the purposes of the present invention, the machine-direction 34 is the direction along which a particular component or material is transported length-wise along and through a particular, local position of the apparatus and method of the invention. The cross-direction 36 lies generally within the plane of the material being transported through the process and is aligned perpendicular to the local machine-direction 34. Accordingly, in the view of the arrangement representatively shown in FIG. 1, the cross-direction 36 extends perpendicular to the plane of the sheet of the drawing.

As representatively shown in FIG. 1, the method and apparatus of the invention can include a transport mechanism, such as provided by the representatively shown transport rollers 14 and their associated power sources (e.g. engines and motors) which can move and direct the web 12 along the appointed machine-direction 34 at a selected transport speed.

In particular aspects, the transport speed can be at least a minimum of about 10 m/min. The transport speed can alternatively be at least about 100 m/min, and optionally, can be at least about 250 m/min to provided improved performance. In other aspects, the transport speed can be not more than a maximum of about 1000 m/min. The transport speed can alternatively be at not more than about 700 m/min, and optionally, can be not more than about 400 m/min to provide improved effectiveness. If the speed is too low, there can be excessively low productivity and high cost. If the speed is too high, any desired transfer of heat to the moving web may be ineffective or insufficient.

As representatively shown in FIG. 1, the transport system can deliver the web 12 to a selected plasticizing mechanism. The delivered web is desirably substantially dry, and the plasticizing mechanism, such as the representatively shown humidifying system, can be configured to operatively increase a ductility or otherwise increase a deformability of the superabsorbent material 32 in the web 12.

For the purposes of the present disclosure, a plasticizing of an appointed material includes any formulation, treatment or technique which operatively reduces stiffness, reduces brittleness and/or reduces rigidity, and allows an operative deformation of the material substantially without an excessive cracking, tearing, splitting, breaking or other fracturing when the material is compressed. The reduction in stiffness, brittleness or rigidity may be temporary or substantially permanent. The non-fracturing deformation may be a resilient deformation, a substantially elastic deformation, or a substantially retained deformation, as well as combinations thereof. The plasticizing of the superabsorbent material may, for example, include a humidification of the material, a heating of the material, a chemical treatment of the material or the like, as well as combinations thereof.

With reference to FIG. 1, the plasticizing of the superabsorbent material 32 within the web 12 can include a mechanism which operatively humidifies the web 12 to a selected extent. For example, in the representatively shown configuration, the web 12 can be transported into a humidifier chamber 16 which operatively exposes the web, particularly the superabsorbent material, to water vapor. The humidification can have an added advantage of providing an increased binding of the superabsorbent to the fibers, especially if the superabsorbent is configured to become tacky during the humidification. The binding can enhance the containment of the particles in their associated matrix material (e.g. fiber matrix or foam matrix) and can provide a more intimate contact between the superabsorbent and the matrix material. As a result, the binding can enhance the liquid-management properties of the absorbent composite web 12.

Various techniques can be employed to operatively humidify the web 12. The techniques can include a high temperature humidification or a low temperature humidification, as well as combinations thereof. Water vapor may be delivered to the web 12 and to the superabsorbent material by exposing the web to humidified air. For example, a vacuum conveyor may be employed to pass the humid air through the web. The humidification may also include a providing of water vapor by employing steam or other high-temperature, moisture-containing, gaseous medium. In additional aspects, the humidification can include a mechanism which generates sufficiently small droplets of water that will readily evaporate to provide the desired concentration of water vapor. For example, a suitable humidification may be accomplished by air showers, misters, atomizers, ultrasonic vaporizers, moisture-condensing devices and the like, as well as combinations thereof. Typically, a driving mechanism (e.g. a fan system or a vacuum system) can be employed to move the humidifying moisture (e.g. water vapor) through the web and into operative contact with the superabsorbent material.

The humidifying of the web 12 can expose the web 12 to a selected concentration of water vapor at a predetermined temperature for a selected length of time. Various mechanisms and techniques can be employed to adjust and regulate the time of exposure. For example, the speed of the web 12 may be increased or decreased to regulate a residence time of the web within the humidifier chamber 16. Alternatively, the path length of the web within the humidifier chamber may be increased or decreased to adjust the residence time. In the shown configuration, for example, a system of festooning rollers 18 may be employed to adjust the web path length within the humidifier chamber 16 to regulate the residence time of the web in the chamber.

The web is desirably subjected to the appointed water vapor concentration (e.g. relative humidity) over a time and a temperature which are sufficient to impart a selected moisture content to the superabsorbent material in the web 12. In particular aspects, the moisture content provided to the superabsorbent can be at least a minimum of about 0.1 grams of water per gram of superabsorbent material (0.1 g/g). The moisture content can alternatively be at least about 0.15 g/g, and optionally, can be at least about 0.2 g/g to provided improved performance. In other aspects, the moisture content can be not more than a maximum of about 0.9 g/g. The moisture content can alternatively be at not more than about 0.6 g/g, and optionally, can be not more than about 0.4 g/g to provide improved effectiveness.

If the moisture content is too low, there can be an excessive generation of dust, an excessive fracturing of the superabsorbent material, or a need for an excessive heating of the web. If the moisture content is too high, there may be excessive adhesion of the web to the manufacturing equipment, there may be excessive disruptions of the manufacturing process, and there may be a reduction of the absorbent capacity of the superabsorbent material.

It has been discovered that the treating of the web 12 with operative levels of water vapor can be more effective than a treating the web with liquid water. When the web is treated with liquid water, the liquid water can primarily be captured or otherwise taken up by the matrix material, such as the fibrous material in the web. As a result, the superabsorbent material may not become adequately plasticized to allow the desired compressing of the web without excessively damaging the properties of the superabsorbent material. Additionally, when liquid water is employed, excessive amounts of water may be needed to generate the desired plasticizing effect on the superabsorbent material, since excessive water may be held by the web matrix material. The excess water can then be difficult and/or expensive to dry or otherwise remove from the web. Accordingly, an aspect of the invention is a substantial avoidance of subjecting the web 12 to excessive amounts of liquid water.

Particular aspects of the invention can include an exposure or other conditioning of the superabsorbent at a relative humidity of up to about 100%. The conditioning relative humidity can be at least a minimum of about 50%, and optionally can be at least about 80% to provide improved performance. Other aspects of the invention can include a conditioning of the superabsorbent at a temperature of up to about 100° C. The conditioning temperature can alternatively be at least a minimum of about 20° C., and optionally, can be at least about 80° C. to provide improved benefits.

In further aspects, the superabsorbent material 32 has been dispensed, deposited or otherwise provided for inclusion in the web 12 at a time and in a condition where the superabsorbent material contains an ambient or first moisture level. The humidifying of the web 12 can then advantageously raise the moisture content of the superabsorbent material to a second level that is above the ambient, first level in the superabsorbent. Then, the compressing of the web can be subsequently conducted when the superabsorbent material contains the second moisture level that is relatively greater than the first moisture level. In other aspects, the process can include a providing a matrix material, such as a fibrous material, for inclusion in the web. The matrix material (e.g. fibers) can, for example, be mixed, layered, bonded, assembled, reacted with, or otherwise combined with the superabsorbent material to form the desired web.

In alternative aspects of the invention, the plasticizing of the superabsorbent material 32 can be accomplished by configuring the superabsorbent material to be in a rubbery, readily deformable state, even when the material is at low humidity levels. Accordingly, the invention can allow a densification of the materials at lower temperatures. The superabsorbent can have a composition which has been chemically processed or otherwise altered to provide a low glass transition temperature in the environment of low relative humidity. Such alteration may include a chemical reaction or treatment which suitably changes the chemistry of the superabsorbent material. In particular aspects, the superabsorbent can have a composition which has been chemically adjusted to provide a glass transition temperature of less than about 35° C. at a relative humidity of 50%.

In other aspects, the superabsorbent material can be treated with an additive to make the superabsorbent rubbery and less susceptible to forming dust. For example, see EP 0 690 077 published Jan. 3, 1996 and entitled HYDROGEL-FORMING POLYMERIC MATERIAL WITH DESIRABLE FRACTURE PROPERTIES. The additive can also operate as a binder material which helps to bind the superabsorbent particles to adjacent fibers. As a result, the plasticizing additive can provide an efficient and distinctive technique for introducing the binder into the absorbent material.

Figure 2:
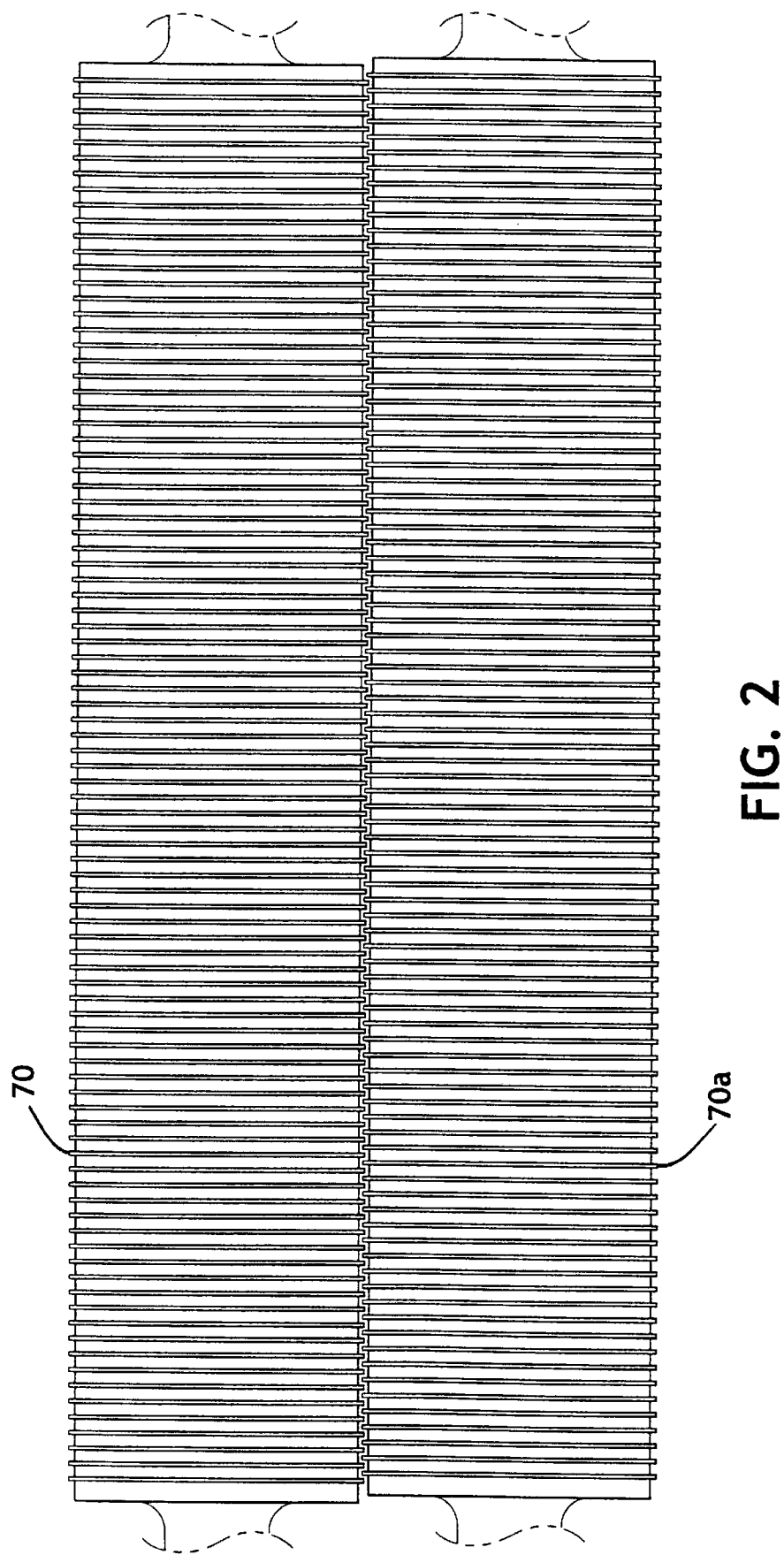
FIG. 2 representatively shows a system of cross-directional softening rollers that can be used with the present invention.
Figure 3:
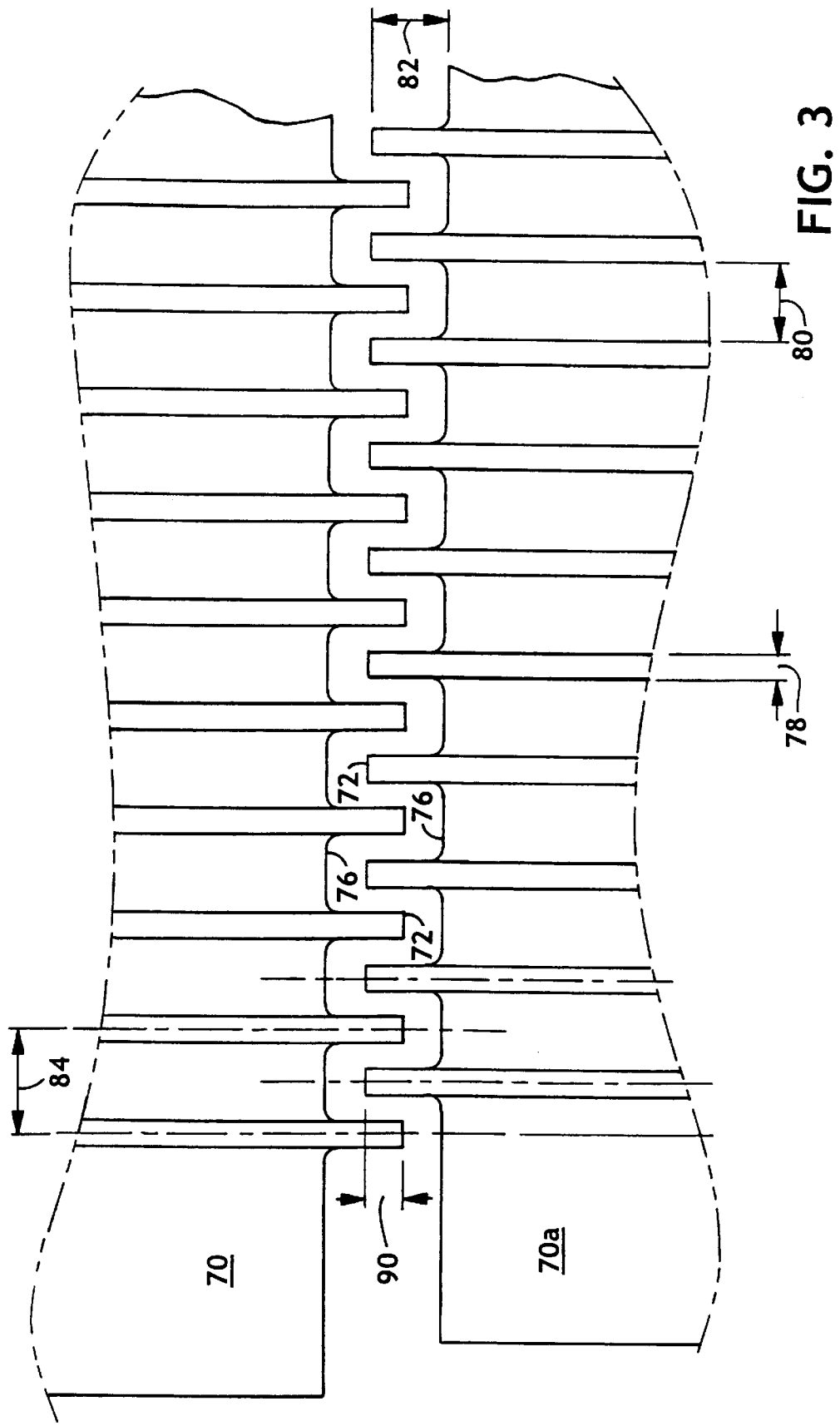
FIG. 3 representatively shows an enlarged view of a portion of the softening rollers illustrated in FIG. 3.
Figure 4:
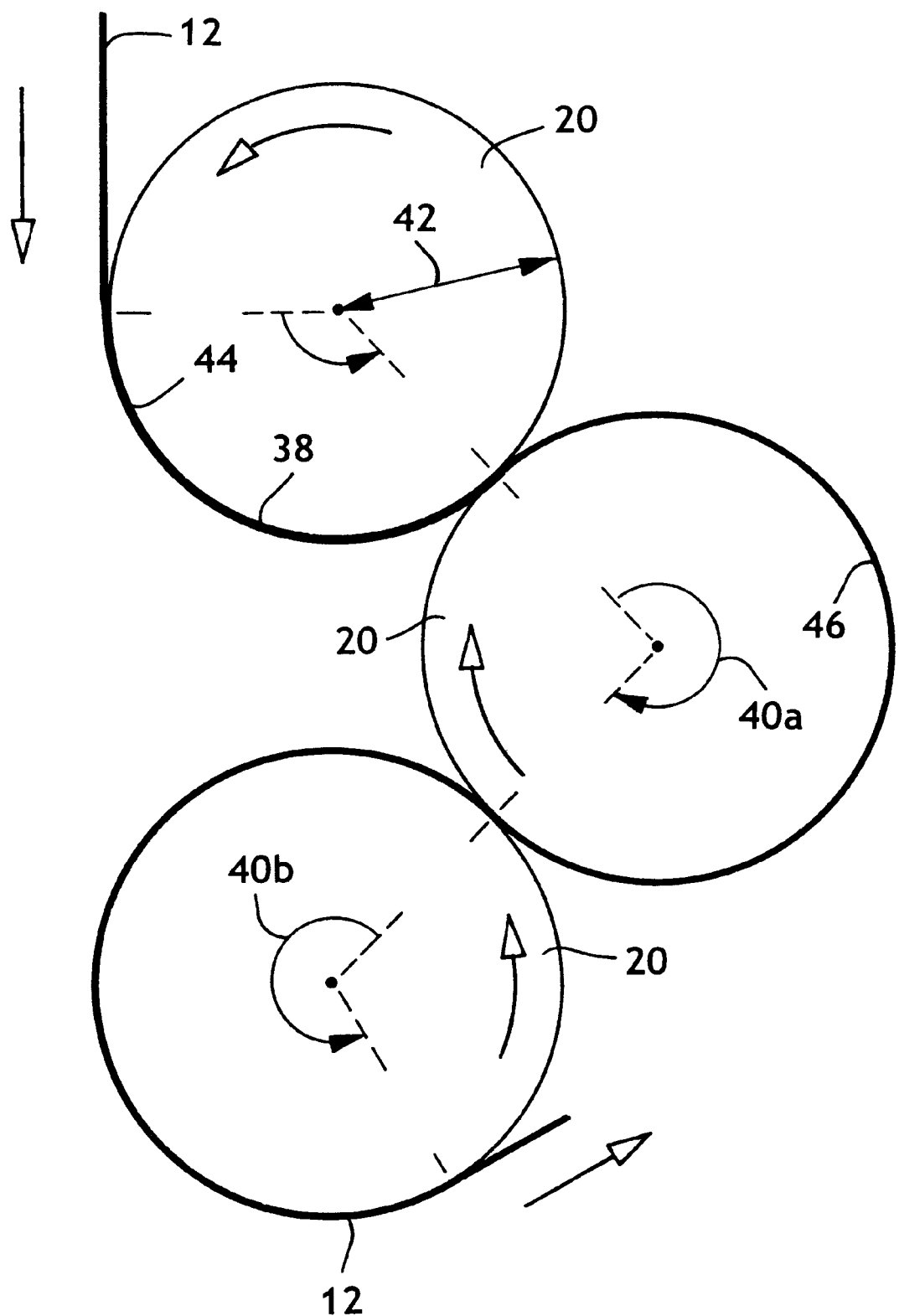
FIG. 4 representatively shows another system of machine-directional softening rollers that can be used with the present invention.

With reference FIGS. 2, 3 and 4, the method and apparatus of the invention can further include a mechanism which provides a predetermined flexing of the web 12. Desirably, the flexing is conducted prior to the compressing of the web. The flexing can advantageously provide a desired unstiffening of the web 12, and the unstiffening can, for example, be conducted prior to, during, or after the humidifying or other plasticizing of the web. The unstiffening of the web can include a selected cross-directional flexing, a machine-directional flexing, or a combination of cross-directional flexing and machine-directional flexing, as desired.

Various techniques can be employed to provide the desired cross-directional flexing of the web 12. For example, the techniques can include embossing, microstraining, biaxial straining and the like, as well as combinations thereof.

Examples of the microstraining technique are described in U.S. Pat. No. 5,562,645 issued Oct. 8, 1996 and entitled ARTICLE WITH SOFT ABSORBENT PULP SHEET by R. W. TANZER et al.

Examples of the biaxial straining technique are described in U.S. Pat. No. 3,902,230 issued Sep. 2, 1975 and entitled SIMULTANEOUS CONTINUOUS BIAXIAL WEB STRETCHER by Schwarz; U.S. Pat. No. 4,223,059 issued Sep. 16, 1980 and entitled PROCESS AND PRODUCT THEREOF FOR STRETCHING A NON-WOVEN WEB OF AN ORIENTABLE POLYMERIC FIBER by Schwarz; and U.S. Pat. No. 4,285,100 issued Aug. 25, 1981 and entitled APPARATUS FOR STRETCHING A NON-WOVEN WEB OR AN ORIENTABLE POLYMERIC MATERIAL by Schwarz.

Other techniques for providing a flexible absorbent material are described in U.S. Pat. No. 4,354,901 issued Oct. 19, 1982 and entitled FLEXIBLE ABSORBENT BOARDS by Kopolow; and U.S. Pat. No. 4,610,678 issued Sep. 9, 1986 and entitled HIGH DENSITY ABSORBENT STRUCTURES by Weisman et al.

With reference to FIGS. 1, 2 and 3, the cross-directional flexing of the web 12 can include a passing of the web through a nip between a pair of cooperating, counter-rotating, circumferentially-grooved rollers 70 and 70a to mechanically flex the web materials with the set of matched grooved rolls. As representatively shown in FIGS. 2 and 3, each of the counter-rotating grooved rollers 70 and 70a can include an alternating series of cooperating peaks 72 and lands 76. The peaks have a selected width 78, and a selected height 82. The lands have a selected width 80 and a selected depth corresponding to the height 82 of the peaks. The adjacent peaks that are on the same roller have a center-to-center distance 84. During operation, the peaks of one roll are substantially centered in the lands of the other, matched roll. An "engagement" distance 90 between the rollers 70 and 70a is measured as the distance from the peak provided by the first roll to the adjacently positioned peak provided by the second roll when the peaks of the first roll penetrate into the grooves of the matched, second roll. A "gap" is measured when the peaks of the first roller do not penetrate into the grooves of the second roller.

In the representatively shown configuration, for example, the width 78 of the peak is 0.031 inch (0.79 mm), and the width 80 of the land is 0.094 inch (2.39 mm). The height 82 of the peak (or equivalently, the depth of the land) is 0.09 inch (2.29 mm). The center-to-center distance 84 between adjacent peaks that are on the same roller is 0.125 inch (3.18 mm).

Examples of suitable circumferentially-grooved rollers are described in U.S. Pat. No. 4,921,643 entitled WEB PROCESSING WITH TWO MATED ROLLS by R. Walton et al., which issued May 1, 1990, the entire disclosure of which is incorporated herein by reference in a manner that is consistent herewith. It should be noted that the retarding fingers described in the U.S. Pat. No. 4,921,543 are not employed in the softening process of the present invention.

When an absorbent layer material or any other web of material travels in a straight direction (linear travel), the velocity of all parts of the material are the same. When the material travels along a curved surface of a roll, the velocity of the material is no longer linear, instead the velocity substantially is circumferential.

The motion of the material along the circumferentially curved path creates a velocity differential such that the average speed of the material is at the center of the thickness of the material. The part of the material which is adjacent to the roll travels at a speed that is slower than the average speed, and the radially, outer most part of the material travels at a speed that is faster than the average speed. To accommodate the velocity differential, the curved material tends to compresses on the concave side of the material, and tends to stretch on the concave side of the material.

The stretching aspect, on the outer, convex side of the material can be particularly helpful for unstiffening the material. The stretching can, for example, pull on the fibers of a fibrous web and break hydrogen bonds (and other bonds) between the fibers. As a result, the material can become more pliable. If one desires to unstiffen only one side of the material web, the geometry of the curved web path can be configured to apply the tension loading and stretching to one appointed side of the web. Running the material through a S-shaped (S-wrap) curved path can tension and stretch each side of the material web in sequence, and can operatively unstiffen and soften both sides of the web.

Applying any kind of tension can help to unstiffen a web material, but by utilizing the bending action around a roll, the degree of unstiffening can be controlled and the strength of the material can be maintained. The bending action can unstiffen the convexly curved portions of the material that are positioned toward the exposed, outward surfaces of the web, while maintaining the strength of the material in the mid-thickness portions of the web that are positioned near the bending, neutral-axis of the curved web.

The extent of the unstiffening (tension) force is typically inversely proportional to the radius of the roll being used. The smaller the diameter of the roll being used, the greater the speed differential and the greater the tension force. The extent of the unstiffening (tension) force is typically directly proportional to the thickness of the absorbent structure. The thicker the material, the greater the speed differential and the greater the tension force.

With reference to FIG. 4, the machine-directional flexing of the web 12 can include a moving of the web along a curved path 38 which curves through a selected, circumferential turning angle 40. In particular aspects, the circumferential turning angle can be at least a minimum of about 15 degrees (15°). The circumferential turning angle can alternatively be at least about 45 degrees, and optionally, can be at least about 90 degrees to provided improved performance. In other aspects, the circumferential turning angle can be up to a maximum of about 270 degrees, or more. The circumferential turning angle can alternatively be at not more than about 240 degrees, and optionally, can be not more than about 200 degrees to provide improved effectiveness.

If the circumferential turning angle is too low, the unstiffening of the web may be insufficient. If the circumferential turning angle is too large, the integrity of the web may be excessively degraded and the processing equipment can become excessively complex.

The curved path 38 can have a selected radius of curvature 42. In particular aspects, the radius of curvature can be at least a minimum of about 1 cm, and alternatively, be at least about 1.5 cm to provided improved performance. In other aspects, the radius of curvature 42 can be not more than a maximum of about 20 cm. The radius of curvature can alternatively be at not more than about 5 cm, and optionally, can be not more than about 2 cm to provide improved effectiveness. If the radius of curvature 42 is too low, there can be an excessive slinging or other loss of superabsorbent material or fiber material out of the web. If the radius of curvature 42 is too large, the level of unstiffening in the web may be insufficient.

With reference to FIG. 4, the machine-directional flexing of the web 12 can include a moving of the web along a substantially S-shaped curved path which curves through a cumulative, reflexed turning angle, such as a reflexed turning angle which includes individual turning angles 40, 40a and 40b. In particular aspects, the cumulative, reflexed turning angle can be up to a maximum of about 2000 degrees, or more. The cumulative, reflexed turning angle can alternatively be up to about 1500 degrees, and optionally, can be up to about 720 degrees to provided improved performance. In other aspects, the cumulative, reflexed turning angle can be not less than a minimum of about 180 degrees. The cumulative, reflexed turning angle can alternatively be at not less than about 270 degrees, and optionally, can be not less than about 360 degrees to provide improved effectiveness.

If the cumulative, reflexed turning angle is too low, the unstiffening of the web may be insufficient. If the cumulative, reflexed turning angle is too large, the processing equipment can become excessively complex.

In the representatively shown configuration, the S-shaped curved path can include a first curved portion 44 and a second, reflexed, oppositely curved portion 46. Each of the first and second curved portions can have any of the radii of curvature and the individual turning angles described herein.

As representatively shown in FIG. 1, the apparatus and method of the invention can further include a selected heating of the web 12. For example, the web 12 can be passed through a nip between a pair of counter-rotating, heated rollers 30 and 30a. As representatively shown, the heater rollers can also be configured to provide a selected compressing and densifying of the web 12. In particular aspects, the heating of the web 12 can be conducted prior to or concurrently with the compressing of the web. In other aspects, the heating of the web can be conducted substantially simultaneously with the compressing of the web. In the various configurations of the invention, the heating of the web 12 can be provided by one or more techniques. Such techniques can include, for example, heating by conduction, radiation, convection or the like, as well as combinations thereof.

In conduction heating, the heat can typically transfer from a region of high temperature to a region of lower temperature within a medium or between mediums that are in direct contact. The conduction heating can, for example, include a heating with heated wrap rollers, heated calender rollers, heated nips, heated dead plates, friction and the like, as well as combinations thereof.

In radiation heating, the heat can typically transfer from a high temperature body to a low temperature body when the bodies are separated by a space. The radiation heating can, for example, include heat lamps which generate infrared radiation, microwave heating, open flames or other combustion, exothermic chemical reactions, heat exchangers and the like, as well as combinations thereof.

Convection heating can typically involve the actions of conduction, energy storage and mixing. The convection heating can, for example, include steam, heated air or other heated gas, and the like, as well as combinations thereof.

Microwave heating can be particularly effective since the superabsorbent material has a natural affinity to water, and the water can be selectively excited and heated with the microwave radiation. The microwave heating can thus bypass the need to transmit the heat energy through any insulating, fibrous material of the web 12. Conduction heating can be less energy efficient because of the need to heat the fibrous material of the web to transfer the heat to the superabsorbent material.

The heating of the web 12 can include a subjecting of the web to a temperature which is at least a minimum of about 20° C. The heating temperature can alternatively be at least about 40° C., and optionally, can be at least about 90° C. to provide improved performance. In other aspects, the heating temperature can be not more than about 205° C. The heating temperature can alternatively be not more than about 175° C., and optionally, can be not more than about 150° C. to provide improved benefits. The heating of the web 12 can help increase the hydrogen bonding of the matrix fibers in the web, and at very high temperatures, the heating can help plasticize the fibers. As a result, less pressure is required to generate the desired density values. The heated fibers have a lower tendency to rebound, and the web is better able to maintain the desired density.

The heating of the web can include a subjecting of the web 12 to a temperature which operatively heats the superabsorbent material of the web to a temperature which within a predetermined percentage of the glass transition temperature (measured in °C.) of the superabsorbent material 32. In particular aspects, the heating temperature can be at least a minimum of about 80% of the glass transition temperature. The heating temperature can alternatively be at least about 90% of the glass transition temperature, and optionally, can be at least about 95% of the glass transition temperature of the superabsorbent material to provide improved efficiency. In other aspects, the heating temperature can be not more than a maximum of about 125% of the glass transition temperature. The heating temperature can alternatively be not more than about 107% of the glass transition temperature, and optionally, can be not more than about 105% of the glass transition temperature of the superabsorbent material to provide improved benefits, such as reduced costs.

If the heated temperature of the superabsorbent material is too high, the material may excessively decompose, or otherwise undergo an undesired chemical change. If the heated temperature of the superabsorbent material is too low, there may be an excessive fracturing of the superabsorbent material.

Conventional techniques for softening an absorbent product, such as described in U.S. Pat. No. 4,605,402 to Iskra, have taught a desired crushing of the superabsorbent to attain the softness in the article. Conventional techniques for densifying absorbent webs using heated calender rolls and high pressures are described in U.S. Pat. No. 5,252,275 and U.S. Pat. No. 5,324,575. Such techniques have been employed to densify webs of crosslinked, high bulk fiber which may contain superabsorbent. The densifying pressures have been in the range of 800–115,000 psi ($5.5 \times 10^3$–$7.9 \times 10^5$ KPa), and the heating temperatures have been between 60° C. and 180° C.

Such high pressures can, however, adversely affect the superabsorbent. In a substantially dry composite, the superabsorbent is typically in a glassy, brittle state and will crack when subjected to high pressures. The cracking of the superabsorbent into smaller particles can be even more detrimental for a surface-crosslinked superabsorbent than for a bulk-crosslinked superabsorbent. With a surface-crosslinked superabsorbent, the cracking of the particles can undesirably expose the more lightly crosslinked material in the center portions of the superabsorbent particles. The surface-crosslinked superabsorbents, however, are preferred for producing thin structures which contain higher amounts of superabsorbent. Examples of such structures are described in U.S. Pat. No. 5,147,343 by Kellenberger; and U.S. Pat. No. 5,601,542 by Melius et al. As a result, the conventional softening and densifying techniques have been inadequate for producing the desired products.

In contrast to the conventional techniques, the compressing mechanism, such as provided by the representatively shown calendering rollers 22, can apply a selective pressure to the web 12 in a manner which operatively reduces the stiffness of the web while substantially avoiding an excessive damaging of the desired properties of the superabsorbent material in the web. In particular, the compressing mechanism can apply a selective pressure to the web 12 in a manner which operatively reduces the bulk of the web while substantially avoiding an excessive fracturing of the superabsorbent material. With reference to FIG. 1, the compressing of the web 12 can include a passing of the web through a nip between a pair of cooperating counter-rotating rollers, such as the representatively shown pair of calendering rollers 22 and 22a. The outer circumferential surfaces of the calendering rollers can be substantially smooth. Alternatively, the outer surfaces of the calendering rollers can be textured. For example, the outer surfaces of the calendering rollers 22 can include a predetermined pattern of circumferentially extending grooves. Alternatively, the surfaces of the calendering rollers can be textured with one or more conventional texturing patterns.

In particular aspects, the compressing of the web 12 can include a subjecting of the web to a selected compressing gap, which can be provided between compression plates, between compression rollers or any other operative compacting mechanism, as well as combinations thereof. The compressing gap can, for example, be selected to be substantially equal to or less than a median particle size of the superabsorbent material. In other aspects of the invention, the compressing gap can be selected to be less than about 2 mm, and may be selected to be less than about 1 mm. The compressing gap can alternatively be less than about 0.6 mm, and optionally, can be less than about 0.3 mm to provide improved benefits. The compressing gap can be generated by employing any convenient technique. For example, the compressing gap may be generated between a pair of pressure plates, or may be generated in the nip area between a cooperating pair of counter-rotating rollers.

In further aspects, the compressing of the web 12 can be configured to provide a compressed web density of at least a minimum of about 0.2 g/cm$^3$. The web density can alternatively be at least about 0.25 g/cm$^3$, and optionally, can be at least about 0.3 g/cm$^3$, or more, to provide improved benefits, such as improved flexibility or improved transport of liquids. In desired arrangements, the web density can be up to about 0.2 g/cm$^3$, or more.

It should be readily appreciated that heated calendering rolls can be employed to both heat and compress the web 12. For example, a compressing and densification of the materials can be accomplished by using induction heated, calendering rolls. The rolls may have a diameter of 9.5 inch (24.1 cm), and may be heated to a temperature of up to about 400° F. (about 205° C). In particular arrangements, the rolls can be operated to provide a speed of about 15 m/min, and can be positioned to provide a selected gap set between the rolls. Optionally, the speed provided by the rolls can be up to 185 m/min, or more. Additionally a selected force can be applied to press one of the rolls against its associated gap stop. Suitable rolls are available from Tokuden Co. a company having offices in Kyoto, Japan; or Tokuden, Inc. a company having offices in Norcross, Ga.

In desired aspects, the web 12 can include a selected combination of fibrous material and superabsorbent material. In desired aspects, the composite material has not been subjected to a fiberizing and/or airlaying procedure during the production of the absorbent web 12. The fibrous material may include absorbent fibers, substantially nonabsorbent fibers, wettable fibers, substantially nonwettable fibers, cellulosic fibers, non-cellulosic fibers, natural fibers, or synthetic fibers, as well as combinations thereof. In particular aspects of the invention the structure of the absorbent web 12 can include at least a minimum of about 0.5 wt % superabsorbent material, as determined with respect to the total weight of the dry absorbent web. In selected products, such as articles configured for feminine care and light incontinence, the absorbent web 12 can alternatively include at least about 0.7 wt % superabsorbent material, and optionally, can include at least about 1 wt % superabsorbent material to provide improved benefits. In other selected products, such as articles configured for infant care diapers, child care training pants, and adult desk incontinence products, the absorbent web can include at least about 15 wt % superabsorbent material, and optionally, can include at least about 30 wt % superabsorbent material to provide improved performance.

In other aspects of the invention, the absorbent web 12 can include not more than a maximum of about 90 wt % of superabsorbent material, as determined with respect to the total weight of the material in the dry absorbent web 12. In selected products, such as articles configured for feminine care and light incontinence, the absorbent web 12 can include not more than about 15 wt % superabsorbent material, and alternatively, can include not more than about 10 wt % superabsorbent to provide improved benefits. Optionally, the absorbent web of such products can include not more than about 5 wt % superabsorbent material to provide desired benefits. In other selected products, such as articles configured for infant care diapers, adult incontinence garments and child care training pants, the absorbent web 12 can include not more than about 70 wt % superabsorbent material, and optionally, can include not more than about 60 wt % superabsorbent material to provide improved performance.

The superabsorbent material employed in the absorbent structures constructed with the present invention can be a polymeric gelling material, and the superabsorbent can be generally in the form of discrete particles. The particles can be of any desired shape, for example, spiral or semi-spiral, cubic, rod-like, polyhedral, at the like. Shapes having a large, greatest-dimension/smallest-dimension ratio, like needles, flakes, and fibers, are also contemplated for use herein. Optionally, conglomerates of particles of absorbent gelling material may also be used in absorbent structures produced with the present invention. Desired for use are particles having an average size of from about 5 microns to about 1 millimeter, and the particles can have various aspect ratios where the aspect ratio is determined by dividing the largest length dimension of the particle by the smallest length dimension of the particle. For a particle with an aspect ratio greater than 5, such as a flake or fiber, the "particle size", as used herein, is the smallest length dimension that bisects a projected view of the individual particle. For a particle with an aspect ratio less than 5, the "particle size" means the largest length dimension that bisects a projected view of the individual particle. After determining the particle sizes, various other parameters or values, such as the median particle size, can be calculated or otherwise determined in a conventional manner.

In desired aspects, the total amount of fiber material in the absorbent web 12 can be at least a minimum of about 10 wt %. The amount of fiber can alternatively be at least about 20 wt %, and optionally, can be at least about 30 wt %. In other aspects, the total amount of fiber material in the absorbent web 12 can be not more than a maximum of about 99.5 wt %. The amount of fiber can alternatively be not more than about 90 wt %, and optionally, can be not more than about 70 wt %.

The material of the absorbent web 12 may or may not include a separately provided binder material, which is additional to the cellulosic fibers and superabsorbent polymer material. The amount of binder material in particular aspects of the invention can be at least about 0.001 wt %, as determined with respect to a total weight of the dry absorbent web. In other aspects, the amount of binder material can be provided in an amount of not more than about 25 wt %.

Where the binder material is a wet-strength agent, the amount of binder material can be at least about 0.002 wt %, and can optionally be at least about 0.05 wt % to provide improved performance. In further aspects, the amount of wet-strength agent can be not more than about 2 wt %. Additionally, the amount of wet-strength agent can alternatively be not more than about 1 wt %, and optionally, can be not more than about 0.07 wt % to provide improved benefits.

Where the binder material is an adhesive binder, the amount of binder material can be at least about 0.05 wt %. The amount of adhesive binder can alternatively be at least about 1 wt %, and optionally, can be at least about 5 wt % to provide improved performance. In additional aspects, the amount of adhesive binder can be not more than about 25 wt %. The amount of adhesive binder can alternatively be not more than about 20 wt %, and optionally, can be not more than about 15 wt % to provide improved benefits.

Where the binder material is an activated binder fiber, such as a thermoplastic fiber or a solvent activated fiber, the amount of binder fiber can be at least about 1 wt %. The amount of binder fiber can alternatively be at least about 1.5 wt %, and optionally, can be at least about 2 wt % to provide improved performance. In additional aspects, the amount of binder fiber can be not more than about 25 wt %. The amount of binder fiber can alternatively be not more than about 15 wt %, and optionally, can be not more than about 5 wt % to provide improved benefits.

Where the binder material is a plasticizer, the amount of plasticizer can be at least about 1 wt %. The amount of plasticizer can alternatively be at least about 1.5 wt %, and optionally, can be at least about 2 wt % to provide improved performance. In additional aspects, the amount of plasticizer can be not more than about 25 wt %. The amount of plasticizer can alternatively be not more than about 15 wt %, and optionally, can be not more than about 5 wt % to provide improved benefits.

Another aspect of the present invention can include an absorbent web 12 which contains stiffened cellulose fibers in an amount which is at least about 20 wt % of the total amount of fibrous material in the absorbent web. The amount of stiffened cellulose fibers can alternatively be at least about 30 wt %, and can optionally be at least about 40 wt % to provide improved performance. In further aspects, the material of the absorbent web 12 can contain stiffened cellulose fibers in an amount which is not more than about 100 wt % of the total amount of fibrous material in the absorbent web. The amount of stiffened cellulose fibers can alternatively be not more than about 70 wt %, and can optionally be not more than about 60 wt % to provide improved performance.

Another aspect of the invention can include an absorbent web 12 which may contain substantially no fiber composed of hydrophilic, crimped, synthetic polymer material. The absorbent web may alternatively contain at least about 5 wt % of hydrophilic, crimped, synthetic fiber, as determined with respect to a total amount of fibrous material in the absorbent web, and may optionally contain at least about 10 wt % of hydrophilic, crimped, synthetic fiber to provide improved performance. In still other aspects, the absorbent web may contain not more than about 50 wt % of hydrophilic, crimped, synthetic fiber. The absorbent web 12 may alternatively contain not more than about 25 wt % of hydrophilic, crimped, synthetic fiber, and may optionally contain not more than about 20 wt % of hydrophilic, crimped, synthetic fiber to provide improved performance. The synthetic fiber can have a fiber length greater than about 2 mm.

In particular aspects of the invention, the web 12 has been wet-formed. In particular aspects, the web 12 has been wet-formed by employing a mixture of the superabsorbent material 32 and the selected fibrous material. For example, the web 12 can be wet-formed by employing a water-containing mixture of the superabsorbent material and the selected fibrous material. In still other aspects, the web 12 can be wet-formed by employing an aqueous, water-containing mixture of the superabsorbent material and the fibrous material, wherein the mixture has been provided in the configuration of a foam. Examples of suitable wet-formed, superabsorbent-containing materials are described in U.S. patent application Ser. No. 09/334,152 entitled AN ABSORBENT ARTICLE WITH AN IMPROVED, WET-FORMED ABSORBENT by S. Melius et al. which was filed Jun. 16, 1999, the entire disclosure of which is incorporated herein by reference in a manner which consistent herewith.

In the various aspects of the invention, the web 12 can be configured to have a basis weight that is sufficient to provide desired levels of performance, such as desired levels of absorbent capacity. In particular aspects, the basis weight can be at least a minimum of about 50 g/m$^2$, and in desired arrangements may be at least about 100 g/m$^2$. The basis weight can alternatively be at least about 400 g/m$^2$, and optionally, can be at least about 750 g/m$^2$ to provided improved performance. In other aspects, the web basis weight can be not more than a maximum of about 1000 g/m$^2$ to provide other desired benefits.

The invention can be configured to provide a selected flexibility value to the web 12. The softness and flexibility of the absorbent material, particularly the wet-formed absorbent material, can be shown by an Edge-wise Compression (EC) value which reflects the softness or stiffness of the dry absorbent material. Accordingly, the Edge-wise Compression value can also reflect the flexibility or stiffness of the absorbent article between the legs of the wearer, and can provide an important indication of desired comfort and fit.

In particular aspects, the absorbent material can have a selected Edge-wise Compression, per basis weight, value (EC value). For various configurations, such as infant care, adult care, feminine care and child care products, the EC value of the absorbent material can be not more than a maximum of about 9 g/gsm, where the basis weight is expressed grams per square meter (gsm, or g/m$^2$). Alternatively, the absorbent material can have a EC value of not more than about 6 g/gsm, and optionally, the absorbent material can have a EC value of not more than about 3 g/gsm to provide improved performance. If the EC value is greater than about 9 g/gsm, the dry absorbent material and the corresponding absorbent article can be too stiff.

For particular configurations, such as infant care and child care products, the absorbent material can have an Edge-wise Compression, per basis weight, value (EC value) of not more than a maximum of about 3 g/gsm, where the basis weight is expressed grams per square meter (gsm or g/m$^2$). Alternatively, the absorbent material can have a EC value of not more than about 2 g/gsm, and optionally, the absorbent material can have a EC value of not more than about 1 g/gsm to provide desired performance. If the EC value for such products is greater than about 3 g/gsm, the dry absorbent material and the corresponding absorbent article can again be too stiff.

In other aspects of the invention, the absorbent material can have an EC divided by basis weight value (EC value) of at least a minimum of about 0.3 g/gsm. Alternatively, the absorbent material can have a EC value of at least about 0.4 g/gsm, and optionally, the absorbent material can have a EC value of at least about 0.5 g/gsm to provide further benefits.

Edge-wise Compression Value

The method by which the Edge-wise Compression (EC) value can be determined is set forth below. A 2 inch by 12 inch (5.1 cm×30.5 cm) piece of absorbent material is cut with its longer dimension aligned with the longitudinal direction of the product or raw material web. The weight of the sample is determined. The thickness of the material is determined under a 0.2 psi (1.38 KPa) load. The material is formed into a cylinder having a height of 2 inches (5.1 cm), and with the two ends having 0–0.125 inch (0–3.18 mm) overlap, the material is stapled together with three staples. One staple is near the middle of the width of the product, the other two nearer each edge of the width of the material. The longest dimension of the staple is in the circumference of the formed cylinder to minimize the effect of the staples on the testing.

An INSTRON tester, or similar instrument is configured with a bottom platform, a platen larger than the circumference of the sample to be tested and parallel to the bottom platform, attached to a compression load cell placed in the inverted position. The specimen is placed on the platform, under the platen. The platen is brought into contact with the specimen and compresses the sample at a rate of 25 mm/min. The maximum force obtained in compressing the sample to 50% of its width (1 inch) (2.54 cm) is recorded.

If the material buckles, it is typical for the maximum force to be reached before the sample is compressed to 50%. In a product where the length of the absorbent is less than 12 inches (30.5 cm), the EC value of the material can be determined in the following manner. A detailed discussion of the edge-wise compression strength has been given in *The Handbook Of Physical And Mechanical Testing Of Paper And Parerboard*, Richard E. Mark editor, Dekker 1983, (Vol. 1). Based on theoretical models governing buckling stresses, in the Edge-wise Compression configuration described, the buckling stress is proportional to $E*t^2/(H^2)$ with the proportionality constant being a function of $H^2/(R*t)$ where E is the Elastic modulus, H is the height of the cylinder, R is the radius of the cylinder, and t is the thickness of the material. Expressing the stress in terms of force per basis weight, it can be shown that the parameter that needs to be maintained constant is $H^2/R$. Therefore, for a sample that is smaller than 12 inches (30.5 cm), the largest possible circle should be constructed and its height (width of the sample being cut out) adjusted such that $H^2/R$ equals 2.1 inches (5.3 cm).

The following Examples are presented to provide a more detailed understanding of the invention, and are not intended to limit the scope of the invention.

EXAMPLES

Wet-laid, superabsorbent-containing, composite materials in the following Examples were prepared with the following technique. The fiber furnish was prepared by hydropulping together the regular and crosslinked, cellulose pulps (bleached southern softwood kraft pulp CR0054 from Kimberly-Clark Corp.; bleached eucalyptus kraft pulp from Aracruz Cellulose SA; and NHB416 crosslinked pulp from Weyerhaeuser Corp.). Generally stated, the hydropulping process includes a dispersing of the fibrous material in water, and an agitation of the resulting mixture. The hydropulping was conducted at an ambient room temperature to a 3% consistency. If a wet-strength agent or binder material, such as KYMENE binder, was added, it was done at the hydropulping stage. For example, KYMENE binder can be added in the amount of 10 pounds of KYMENE binder solids per 1 metric ton of furnish. Because of the difficulty of opening the crosslinked fibers, the hydropulping was normally done for one hour. A suitable device for hydropulping the fibrous materials is a 10 gallon, laboratory model, hydropulper available from Adirondack Machine Corp, a business having offices located in Glen Falls, N.Y., or a substantially equivalent system.

The handsheets were formed using a SERIES 9000 computerized handsheet former, available from M/K Systems, a business having offices in Danvers, Mass. The forming wire fabric in the forming chamber of the handsheet former was composed of 90×90 mesh, stainless steel.

The handsheet forming process included a pumping of about one gallon of fresh water into the forming chamber (about 1 second of flow). Sufficient furnish was pumped into the forming chamber to provide the final handsheet (with superabsorbent) with a basis weight of about 400 gsm (g/m²). Additional water was added to dilute the resulting stock. If it was desirable to slow the swelling of the superabsorbent polymer (SAP) material, this additional water was composed of ice water (at a temperature of 2° C.). The fiber was thoroughly agitated in the forming chamber, and superabsorbent polymer material was added during the agitation. The addition of the superabsorbent occurred at the beginning of the agitation, if a large amount of superabsorbent swelling was desirable; and occurred near the end of the agitation, if a small amount of superabsorbent swelling was desirable. The contents of the forming chamber were allow to settle for 2 seconds, and were then drained. The resulting sheet was de-watered, and then dried at a temperature of 105° C.

Sheets with sufficiently high integrity could be automatically de-watered by the former, then picked off the felt in the former and placed on a stainless steel screen for oven drying. The sheets can, for example, be de-watered with a vacuum de-watering system.

Sheets which did not have enough integrity to be automatically de-watered were handled manually. During the manual handling, the automated process was paused at the drainage stage, and the handsheet was further consolidated with blotters and a rolling weight. The sheet was then transferred by hand from the forming screen directly onto a drying screen.

Examples of wet, foam-formed composite materials constructed from a foamed fiber slurry were produced with the following technique. The foam-forming technique employed the equipment and procedures employed to produce the wet-laid absorbent composite materials, except that at the stage where the fiber slurry is agitated in the forming chamber, the equipment was placed on hold—that is the agitation was continued until a command was entered to stop it. Particulate superabsorbent polymer material was added to the forming chamber, followed by an addition of 9.5 wt % of surfactant, based on the combined dry weight of fiber and superabsorbent. The surfactant used was REXENE KB obtained from ICI Surfactants, a business having offices located in Wilmington, Del. The resultant superabsorbent polymer and fiber slurry foamed vigorously due to the air bubble agitation. A hand mixer was used to break the large bubbles into a finer, more uniform foam. When the slurry appeared stable (after approximately 45 seconds of agitation), drainage was begun. The formed sheet was extremely weak and was lifted off the wire by sliding a sheet of polypropylene spunbonded fabric between the wire and the composite and using this fabric to support the formed sheet during the transfer to a drying rack. Drying was conducted at a temperature of 105° C., as noted above for the wet-laid absorbent materials.

In many of the examples, the various wet-formed samples, as prepared, were too stiff for purposes of the present invention. Accordingly, the excessively stiff materials were further modified by various softening methods. These methods included a humidification of the materials, a mechanical softening through a nip between a pair of matched grooved rolls, and/or a compressing of the materials through a nip between a pair of heated calendering rollers, as well as various combinations of these methods.

Samples that were humidified were placed in a controlled humidity chamber at 80% Relative Humidity and 100° F. (38° C.) for 24–65 hours, then conditioned at 50%±2% relative humidity, and 73.4° F.±1.8° F. (23° C.±1° C.). Resulting moisture pickup after conditioning is noted in TABLES 4 and 5.

The mechanical flexing of the materials can be achieved with a set of matched grooved rolls 70 and 70a. As representatively shown in FIGS. 2 and 3, each of the counter-rotating grooved rollers 70 and 70a includes an alternating series of cooperating peaks 72 and lands 76. The width 78 of the peak is 0.031 inch (0.79 mm), the width 80 of the land is 0.094 inch (2.39 mm). The height 82 of the peak (or equivalently, the depth of the land) is 0.09 inch (2.29 mm). The center-to-center distance 84 between adjacent peaks that are on the same roller is 0.125 inch (3.18 mm). The peaks of one roll are substantially centered in the lands of the other, matched roll. The "engagement" 90 between the rollers 70 and 70a is measured as the distance from the peak provided by the first roll to the adjacently positioned peak provided by the second roll when the peaks of one roll penetrate into the grooves of the matched roll. A "gap" is measured when the peaks of one roller do not penetrate into the grooves of the second roller. The amount of engagement between the grooves of the softening rolls is indicated in TABLES 2 an 5.

A compressing and densification of the materials was accomplished using a pair of induction heated, calendering rolls of 9.5 inch (24.13 cm) diameter, at a speed of 50 ft/min (15.24 m/min), at a temperature of 220–225° F. (104–107° C.), and with the gap between the rolls set as specified in TABLES 3 and 5. The samples were between 6 and 7 inches (15.2 cm–17.9 cm) in width along the axial length of the rolls. The pressure applied to the rolls and the weight of the rolls themselves resulted in a force of 4380 lb (1987 kg) on the samples. The resulting gap when the sample was passed through the calender was not measured. It would be equivalent to or larger than the gap that was set prior to calendering. If the pressure provided by the rolls was insufficient to prevent the rolls from lifting off their associated gap stops, the resulting gap would be larger. Suitable calendering rolls are available from Tokuden Co. a company having offices in Kyoto, Japan; or Tokuden, Inc. a company having offices in Norcross, Ga.

EXAMPLES 1A through 16B

The superabsorbent (SAP) used for all of the Examples was FAVOR SXM 880 superabsorbent available from Stockhausen, Inc. Where a KYMENE binder was employed, the binder was KYMENE 557LX available from Hercules, Inc. of Wilmington, Del. The KYMENE binder was used in the amount of 10 pounds of KYMENE binder solids per 1 metric ton of furnish for all Examples; except for Examples 13A, 13B, 13C and 13D, in which the KYMENE binder was not added. A BEROCEL 596 debonding agent, available from Eka Chemicals, a business having offices located at Marietta, Ga., was used in Example 4A only. The BEROCEL debonding agent was added to the mixture before agitation by employing an air stream blown into the forming chamber.

Examples 1A through 6A were made according to the above-described procedure using room temperature water. Examples 7A through 15A were made according to the above procedure using ice water to slow the swelling of the superabsorbent. Example 16A is an example of a wet-formed material produced with the foamed fiber slurry process.

TABLE 1 shows the composition and resulting Edge-wise Compression value and density of the listed examples. Examples 1A and 4A are examples that would be useful in the present invention. The other examples are given for the purposes of comparison to the modified materials, as described in TABLES 2, 3, 4, and 5.

TABLE I

| Example | SAP % | NHB416 % | CR0054 % | Eucalyptus % | EC Value (g/gsm) | DENSITY (g/cm³) |
|---|---|---|---|---|---|---|
| 1A | 60 | 22 | 18 | 0 | 5.97 | 0.08 |
| 2A | 40 | 33 | 27 | 0 | 11.1 | 0.07 |
| 3A | 25 | 41.25 | 33.75 | 0 | 19.05 | 0.07 |
| 4A | 24 | 22.8 | 53.2 | 0 | 7.06 | 0.05 |
| 5A | 24 | 22.8 | 53.2 | 0 | 12.64 | 0.07 |
| 6A | 15 | 46.75 | 38.25 | 0 | 25.75 | 0.06 |
| 7A | 60 | 18 | 22 | 0 | 11.14 | 0.09 |

TABLE I-continued

| Example | SAP % | NHB416 % | CR0054 % | Eucalyptus % | EC Value (g/gsm) | DENSITY (g/cm³) |
|---|---|---|---|---|---|---|
| 8A | 60 | 22 | 18 | 0 | 19.14 | 0.1 |
| 9A | 40 | 60 | 0 | 0 | 12.27 | 0.07 |
| 10A | 40 | 36 | 24 | 0 | 26.44 | 0.09 |
| 11A | 40 | 27 | 33 | 0 | 25.15 | 0.08 |
| 12A | 40 | 0 | 60 | 0 | 34.88 | 0.09 |
| 13A | 40 | 0 | 60 | 0 | 21.86 | 0.08 |
| 14A | 40 | 0 | 0 | 60 | 18.92 | 0.09 |
| 15A | 40 | 0 | 30 | 30 | 32.13 | 0.12 |
| 16A | 25 | 22.5 | 52.5 | 0 | 4.52 | 0.05 |

TABLE 2 shows the effect of softening of the materials with matched grooved rolls: The unsoftened material (designated with a suffix "A") is shown for comparison to the softened material (designated with a suffix "B", "C" or "D").

TABLE 2

| Example | Softening Roll Engagement (mm) | Number of passes through Softening Roll | EC Value (g/gsm) | DENSITY (g/cm³) |
|---|---|---|---|---|
| 1A | — | — | 5.97 | 0.08 |
| 1B | 0.762 | 1 | 1.78 | 0.15 |
| 1C | 1.016 | 1 | 1.83 | 0.16 |
| 1D | 1.270 | 1 | 1.66 | 0.16 |
| 2A | — | — | 11.1 | 0.07 |
| 2B | 1.270 | 1 | 3.39 | 0.14 |
| 2C | 1.778 | 1 | 3.68 | 0.15 |
| 7A | — | — | 11.14 | 0.09 |
| 7B | 1.270 | 1 | 3.41 | 0.18 |
| 8A | — | — | 19.14 | 0.1 |
| 8B | 1.270 | 1 | 7.07 | 0.16 |
| 9A | — | — | 12.27 | 0.07 |
| 9B | 1.270 | 1 | 5.77 | 0.13 |
| 10A | — | — | 26.44 | 0.09 |
| 10B | 1.778 | 1 | 8.03 | 0.17 |
| 13A | — | — | 21.86 | 0.08 |
| 13B | 1.778 | 1 | 7.6 | 0.19 |
| 14A | — | — | 18.92 | 0.09 |
| 14B | 1.778 | 1 | 3.68 | 0.14 |
| 14C | 1.778 | 2 | 1.43 | 0.16 |

TABLE 3 shows the effect of softening by Heated Calendering. The unsoftened material (designated with the suffix "A") is shown for comparison to the softened material.

TABLE 3

| Example | Calender Gap (mm) | EC Value (g/gsm) | DENSITY (g/cm³) |
|---|---|---|---|
| 4A | — | 7.06 | 0.05 |
| 4B | 1.016 | 4.65 | 0.1 |
| 4C | 0.762 | 3.95 | 0.13 |
| 5A | — | 12.64 | 0.07 |
| 5B | 1.016 | 8.3 | 0.12 |
| 5C | 0.762 | 7.46 | 0.15 |
| 16A | — | 4.52 | 0.05 |
| 16B | 0.762 | 2.27 | 0.15 |

TABLE 4 shows softening by humidification. The unsoftened material (having the suffix "A") is shown for comparison to the softened material.

TABLE 4

| Example | Moisture Pickup (wt %) | EC Value (g/gsm) | DENSITY (g/cm³) |
|---|---|---|---|
| 1A | — | 5.97 | 0.08 |
| 1E | 3 | 3.37 | 0.08 |

TABLE 5 shows softening by a combination of methods. The unsoftened material (designated with the suffix "A") is shown for comparison to the softened material. A dash ("-") in the table means that the softening process was not done on that example. Where samples were subjected to multiple softening steps, the steps were conducted in the order (from left to right) listed in the Table (e.g. humidified, softening rolls, heated calender rolls).

TABLE 5

| Example | Moisture Pickup (wt %) | Softening Roll Engagement (mm) | Number of passes through Softening Roll | Calender Gap (mm) | EC Value (g/gsm) | DENSITY (g/cm³) |
|---|---|---|---|---|---|---|
| 1A | — | — | — | — | 5.97 | 0.08 |
| 1F | 3 | 0.762 | 1 | — | 2.51 | 0.17 |
| 1G | 3 | 1.016 | 1 | — | 1.4 | 0.18 |
| 1H | 5 | — | — | 0.762 | 2.99 | 0.26 |
| 1I | 5 | — | — | 1.016 | 2.26 | 0.26 |
| 2A | — | — | — | — | 11.1 | 0.07 |
| 2D | 5 | 0.762 | 1 | — | 5.82 | 0.15 |
| 2E | 5 | 1.270 | 1 | — | 5.94 | 0.17 |
| 2F | 5 | — | — | 1.270 | 4.64 | 0.19 |
| 3A | — | — | — | — | 19.05 | 0.07 |
| 3B | 11 | 0.762 | 2 | — | 5.34 | 0.17 |
| 3C | 11 | 1.778 | 2 | — | 4.37 | 0.19 |
| 4A | — | — | — | — | 7.06 | 0.05 |
| 4D | 0.3 | — | — | 1.016 | 2.21 | 0.11 |
| 4E | 0.3 | — | — | 0.762 | 2.36 | 0.16 |
| 5A | — | — | — | — | 12.64 | 0.07 |
| 5D | 1 | — | — | 1.016 | 4.15 | 0.13 |
| 5E | 1 | — | — | 0.762 | 4.54 | 0.16 |
| 6A | — | — | — | — | 25.75 | 0.06 |
| 6B | 9 | 0.762 | 2 | — | 8.12 | 0.17 |
| 6C | 9 | 1.778 | 2 | — | 5.53 | 0.18 |
| 7A | — | — | — | — | 11.14 | 0.09 |
| 7C | 18 | 1.270 | 1 | — | 3.02 | 0.19 |
| 8A | — | — | — | — | 19.14 | 0.1 |
| 8C | 18 | 1.270 | 1 | — | 5.5 | 0.2 |
| 9A | — | — | — | — | 12.27 | 0.07 |
| 9C | 6 | 1.270 | 1 | — | 3.66 | 0.18 |
| 9D | 6 | 1.270 | 1 | 1.270 | 3.69 | 0.19 |
| 10A | — | — | — | — | 26.44 | 0.09 |
| 10C | 10 | 1.778 | 1 | — | 6.79 | 0.18 |
| 11A | — | — | — | — | 25.15 | 0.08 |
| 11B | 14 | 1.778 | 1 | — | 6.85 | 0.19 |
| 12A | — | — | — | — | 34.88 | 0.09 |
| 12B | 7 | 1.778 | 1 | — | 8.5 | 0.21 |
| 13A | — | — | — | — | 21.86 | 0.08 |
| 13C | 6 | 1.778 | 1 | — | 6.19 | 0.22 |
| 13D | 6 | 1.778 | 1 | 1.270 | 6.26 | 0.23 |
| 14A | — | — | — | — | 18.92 | 0.09 |
| 14D | 7 | 1.778 | 1 | — | 5.18 | 0.17 |
| 14E | 7 | 1.016 | 2 | — | 2.69 | 0.16 |
| 15A | — | — | — | — | 32.13 | 0.12 |
| 15B | 6 | 1.270 | 2 | — | 6.75 | 0.19 |
| 15C | 6 | 1.778 | 2 | — | 5.41 | 0.2 |

Incorporated. For the superabsorbent testing, a sample was taken from granules that pass through a U.S. standard 30 mesh sieve and are retained on a U.S. standard 50 mesh sieve (300–600 microns nominal size range).

The as-received superabsorbent samples 18A through 18C were kept in a controlled humidity environment at a 50% Relative Humidity (RH), and 23° C. temperature. The lower moisture samples 17A through 17C were prepared by thinly spreading a quantity of the superabsorbent in a shallow pan, and placing each sample in a temperature controlled room at a relative humidity of less than 20% and a temperature of 130° F. (54° C.) for 27 hours. The higher moisture samples 19A through 19C were prepared by placing each sample in a humidity controlled room at a 80% RH, and 100° F. (38° C.) temperature for 3 hours.

After conditioning the superabsorbent to the selected moisture levels, an individual test sample was prepared by spreading a 1 gram quantity of superabsorbent over an area of about 45.6 cm², onto a piece of weighing paper. A suitable weighing paper is Baxter Scientific Products, S/P brand weighing paper, catalog number B2040-2, measuring 4 inch×4 inch (10.2 cm×10.2 cm), which is available from EXAMPLES 17A through 19C In Examples 17A through 19C, the superabsorbent material used was FAVOR SXM 880 obtained from Stockhausen, Baxter Healthcare Corp, McGaw Park, Ill. A second piece of weighing paper was placed on top of the superabsorbent, and the assembled sample was placed onto the bottom plate of a flat Carver press. Shims of 0.127 mm thickness were placed on the bottom plate to provide gap-stops. Accordingly, when the top and bottom plates of the Carver press contacted the shims, the gap between the plates was 0.127 mm. A suitable press is a Carver laboratory Press Model 25-15HC (Catalog No. 3977), available from Fred S. Carver, Inc., Wabash, Ind.

Each compressed sample was compacted for 10 seconds with a force of 10,000 pounds (44,450 N). Samples 17A, 18A and 19A were compressed at room temperature (73° F.). Samples 17B, 18B and 19B were tested with the Carver press plates at a temperature of 200° F. For the higher temperature samples, each samples was left on the bottom plate for about 30 seconds prior to compression to ensure they were near the temperature of the plates.

Figure 5:
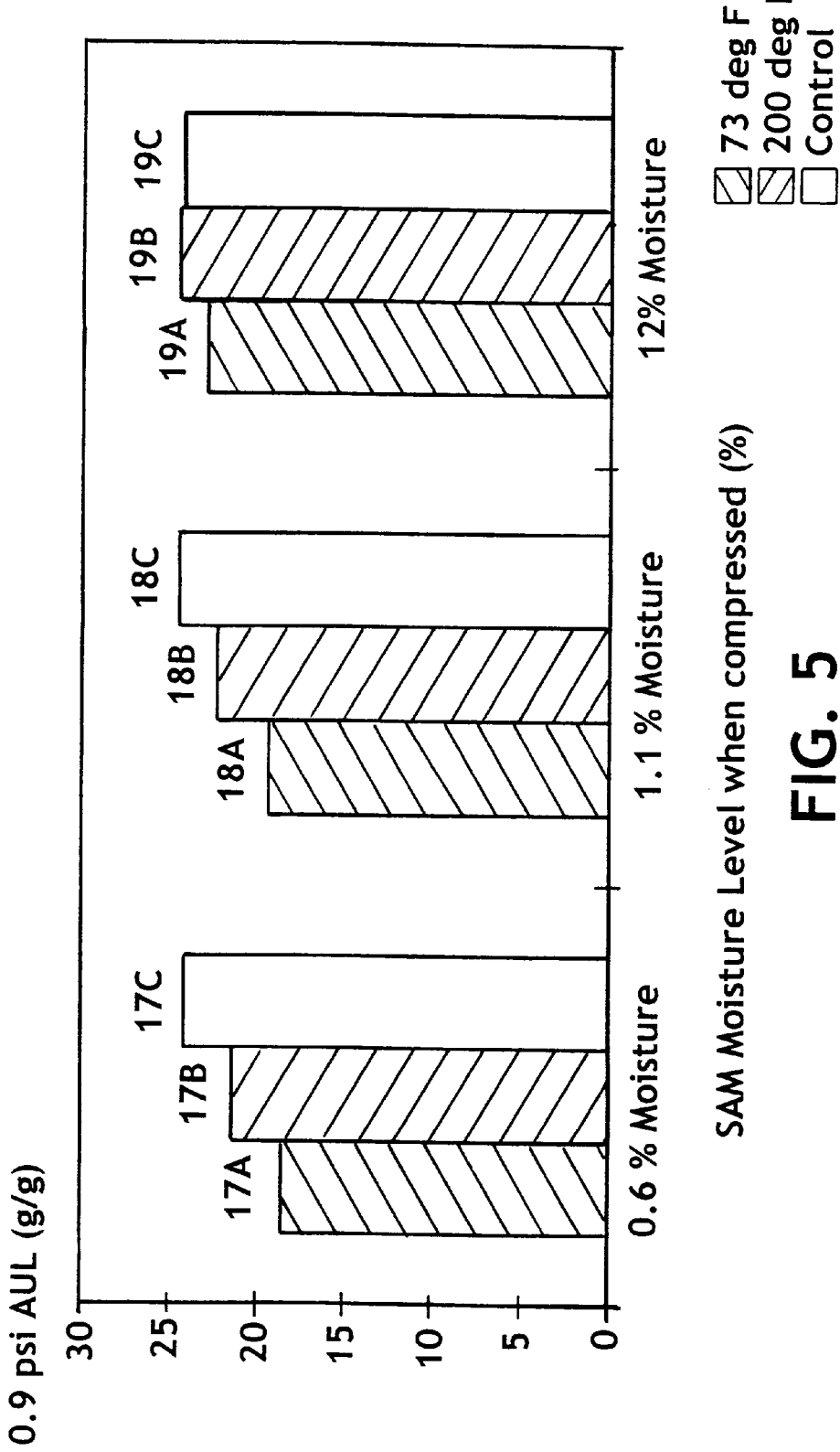
FIG. 5 is a graph which representatively shows the difference in the Absorbency Under Load performance parameter of a number of samples of superabsorbent material, where the various samples of superabsorbent material have been subjected to different conditions of compressing pressure, temperature and moisture content.

The superabsorbent in each sample was conditioned at a 50% RH and a 23° C. temperature prior to Absorbency-Under-Load (AUL) testing. Moisture levels were determined after conditioning to convert absorbency calculations to a dry weight basis. The resulting data are summarized in TABLE 6, and in the graph of FIG. 5.

TABLE 6

Compressed Superabsorbent Samples
Effect of Temperature and Pressure On Absorbency
Under Load at 0.9 psi (6.2 KPa)

| Sample | Moisture when compressed (wt %) | Temperature When Compressed | AUL (grams of saline per gram dry superabsorbent) |
|---|---|---|---|
| 17A | 0.6 | 73° F. (23° C.) | 18.5 |
| 18A | 1.1 | 73° F. (23° C.) | 19.3 |
| 19A | 12.0 | 73° F. (23° C.) | 22.9 |
| 17B | 0.6 | 200° F. (93° C.) | 21.3 |
| 18B | 1.1 | 200° F. (93° C.) | 22.1 |
| 19B | 12.0 | 200° F. (93° C.) | 24.4 |

Uncompressed samples (controls) were conditioned to the three described moisture levels, but were not compressed. The samples of the control superabsorbent were then conditioned at a 50% RH and a 23° C. temperature prior to AUL testing, and moisture levels were determined after conditioning to convert absorbency calculations to a dry weight basis. The resulting data are summarized in TABLE 7, and in the graph of FIG. 5.

TABLE 7

Uncompressed Superabsorbent Samples
Absorbency Under Load at 0.9 psi (6.2 KPa)
for "Control" Superabsorbent

| Sample | Moisture (wt %) | AUL (grams of saline per gram dry superabsorbent) |
|---|---|---|
| 17C | 0.6 | 24.2 |
| 18C | 1.1 | 24.4 |
| 19C | 12.0 | 24.3 |

It can be seen that when no heat or moisture is added to the superabsorbent material, the as-received superabsorbent can suffer significant damage when it is compressed. For example, the compressed as-received sample (e.g. Sample 18A) exhibited a degraded, low AUL value, as compared to its control sample (e.g. Sample 18C). Additionally, it can be seen that reducing the moisture content in the superabsorbent has a small effect on the superabsorbent properties. For example, the compressed, low-moisture superabsorbent (e.g. Sample 17A) provided AUL values that are similar to, but less than, the AUL values provided by the compressed, as-received superabsorbent (e.g. Sample 18A).

Increasing the moisture content without adding heat can help to reduce damage to the superabsorbent. For example, the compressed high-moisture sample (e.g. Sample 19A) exhibited a higher AUL value than the compressed low-moisture sample (e.g. Sample 17A). Adding heat without increasing the moisture content can also help to reduce damage to the superabsorbent. For example, the compressed high-temperature sample (e.g. Sample 18B) exhibited a higher AUL value than the compressed low-temperature sample (e.g. Sample 18A).

Increasing both the moisture content and the temperature of the superabsorbent, however, can advantageously result in substantially no damage to the superabsorbent material. For example, the compressed high-moisture-high-temperature sample (e.g. Sample 19B) provided a similar AUL as its control sample (e.g. Sample 19C).

EXAMPLE 20

Samples of 27 composites were constructed to include superabsorbent and woodpulp fluff fibers. The composites were airformed in a substantially homogeneous mixture with a nominal total basis weight of 400 g/m$^2$. 40 wt % of the composite was superabsorbent, and 60 wt % was woodpulp fibers. The superabsorbent was FAVOR SXM 880, obtained from Stockhausen, Incorporated, and the pulp was CR 1654, a bleached southern softwood kraft pulp obtained from Kimberly-Clark Corp. The composite samples were conditioned in controlled temperature and humidity environments to provide the desired moisture levels in the composites. The composites were then compacted between a pair of compression rollers at selected pressures in the manner described for Examples 1A–16A. The compressing force was applied to the rolls when the rolls were at an initial gap of zero. The composites measured 8 inches (20.3 cm) in width along the axial dimension of the compression rollers. The compacting parameters and the resulting density data are summarized in TABLES 8, 9 and 10.

TABLE 8

Density of Compressed Composite (g/cm$^3$)

| Temperature of compression rollers 75° F. (24° C.) Compression (Newtons per linear meter) | Moisture Content of Composite | | |
|---|---|---|---|
| | 0.65 wt % | 10.5 wt % | 35.3 wt% |
| 1000 | 0.11 | 0.14 | 0.18 |
| 5400 | 0.16 | 0.24 | 0.29 |
| 9800 | 0.21 | 0.31 | 0.39 |

TABLE 9

Density of Compressed Composite (g/cm³)

| Temperature of compression rollers 200° F. (93° C.) Compression | Moisture Content of Composite | | |
|---|---|---|---|
| (Newtons per linear meter) | 0.65 wt % | 10.5 wt % | 35.3 wt% |
| 1000 | 0.12 | 0.14 | 0.22 |
| 5400 | 0.17 | 0.25 | 0.37 |
| 9800 | 0.22 | 0.33 | 0.43 |

TABLE 10

Density of Compressed Composite (g/cm³)

| Temperature of compression rollers 300° F. (149° C.) Compression | Moisture Content of Composite | | |
|---|---|---|---|
| (Newtons per linear meter) | 0.65 wt % | 10.5 wt % | 35.3 wt% |
| 1000 | 0.12 | 0.15 | 0.21 |
| 5400 | 0.18 | 0.3 | 0.38 |
| 9800 | 0.23 | 0.38 | 0.5 |

TABLES 8 through 10 show that increasing the temperature of the compression rollers to increase the temperature of the superabsorbent material in the composite can help to increase the compressed density of the composite when the compacting is conducted at a given pressure. In addition, the TABLES show that increasing the moisture content of the composite to increase the moisture level in the superabsorbent material can help to increase the compressed density of the composite when the compacting is conducted at a given temperature. Accordingly, a target density can be achieved at a lower pressure by adding heat and/or moisture to the composite. The resulting plasticization of the superabsorbent material and the lower pressure employed during compacting can substantially avoid excessive damage to the superabsorbent material.

EXAMPLES 21–23

Figure 6:
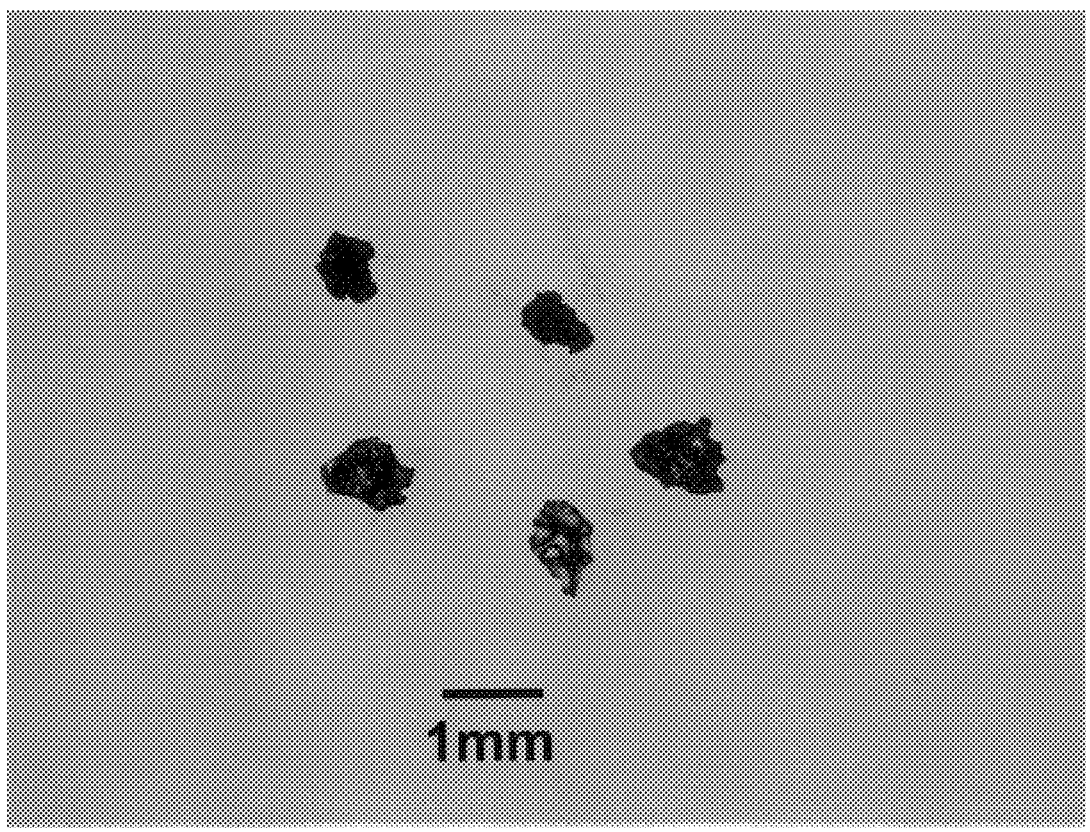
FIG. 6 representatively shows a magnified top view of a quantity of relatively dry superabsorbent material prior to compressing.
Figure 6A:
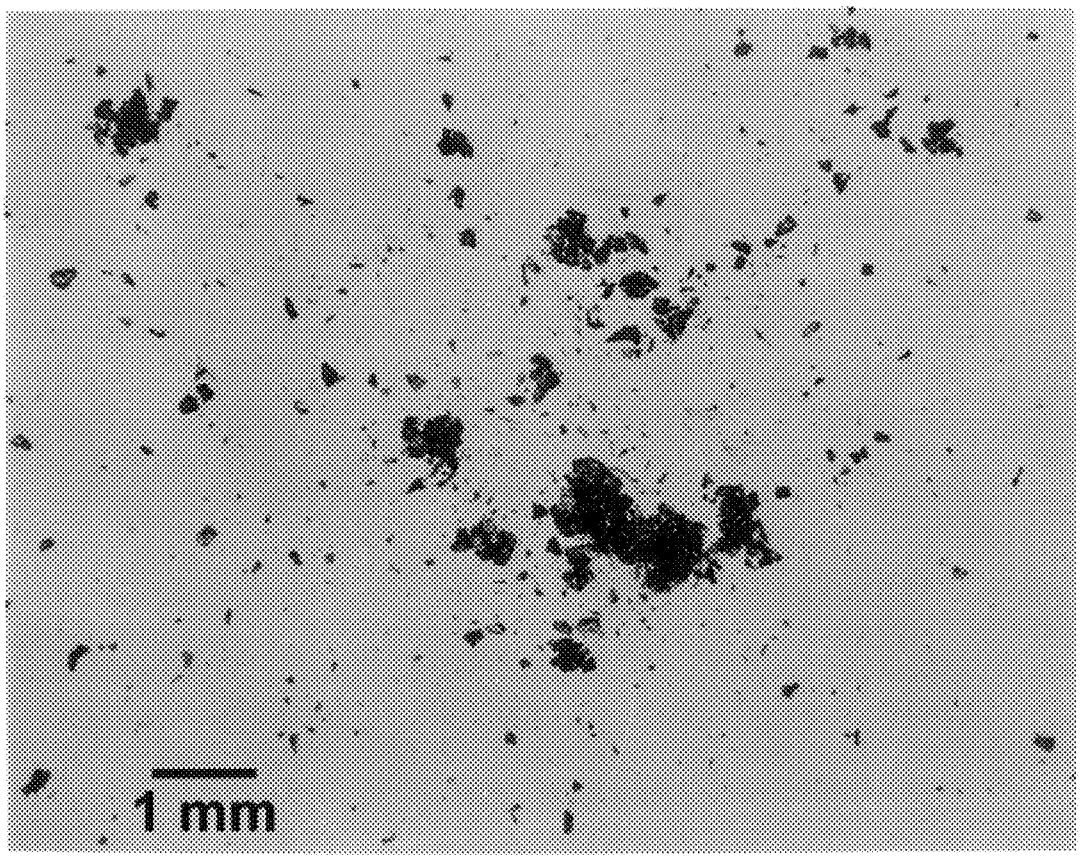
FIG. 6A representatively shows a magnified top view of the superabsorbent material of FIG. 6 after the superabsorbent has been compressed under low force, wherein the superabsorbent particles have been damaged and fractured.

Samples of FAVOR 880 superabsorbent material having a 300 μm–600 μm particle size range were examined to determine the effects of compressive forces on the superabsorbent. With reference to FIGS. 6 and 6A, a first sample (Example 21) was composed of particles of dry superabsorbent material. The sample was placed between a pair of glass microscope slides, and the slides were pressed together with a mild, finger-applied force to compact the superabsorbent. FIG. 6 shows the superabsorbent particles prior to compression, and FIG. 6A shows that the compression readily shattered the superabsorbent particles.

Figure 7:
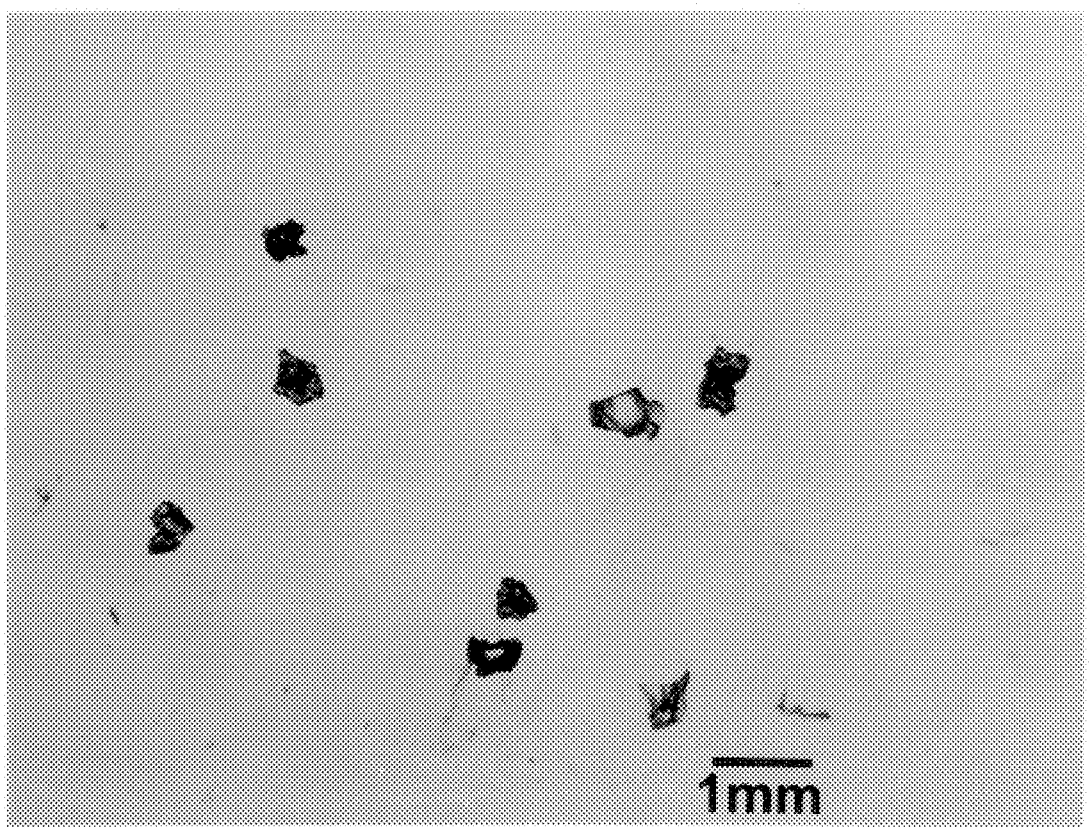
FIG. 7 representatively shows a magnified top view of a quantity of relatively dry superabsorbent material conditioned at approximately 50% relative humidity prior to compressing.
Figure 7A:
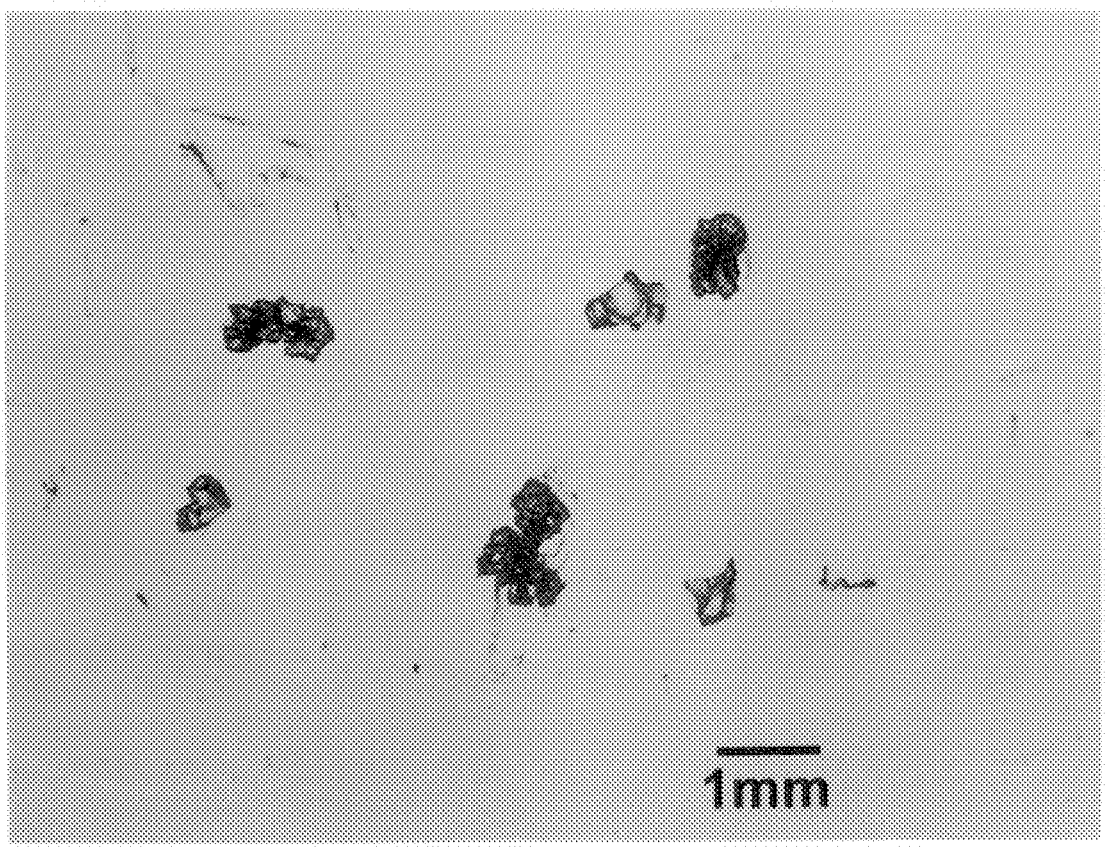
FIG. 7A representatively shows a magnified top view of the superabsorbent material of FIG. 7 after the superabsorbent has been compressed to a 50 μm gap.

A second sample (Example 22) was composed of particles of superabsorbent material which had been conditioned in an environment having a 50% RH and a 23° C. temperature. With reference to FIGS. 7 and 7A, the sample was placed between a pair of glass microscope slides and the slides were forced together. An increased force was required to press the slides to a gap of 50 μm to compact the superabsorbent. FIG. 7 shows the superabsorbent particles prior to compression, and FIG. 7A shows that, after compression, the superabsorbent in this sample had been able to withstand the greater applied pressure with minimal breakage.

Figure 8:
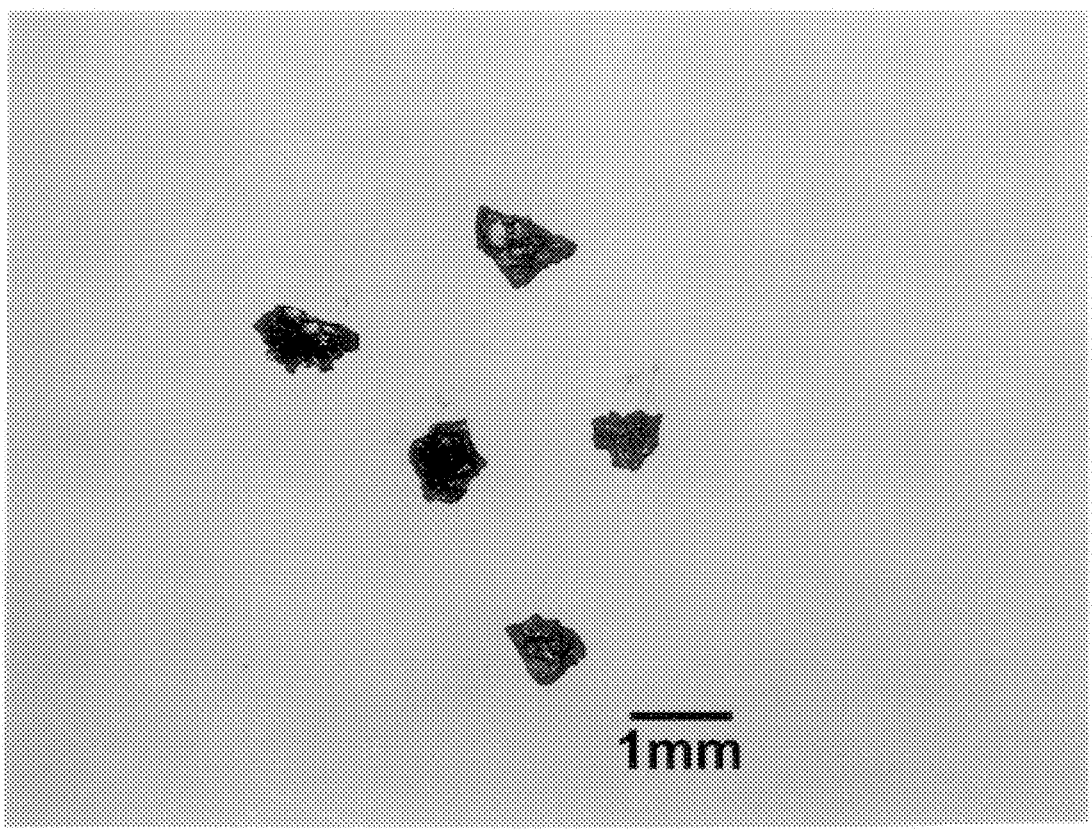
FIG. 8 representatively shows a magnified top view of a quantity of relatively dry superabsorbent material prior to conditioning at approximately 80% relative humidity and 100° F.
Figure 8A:
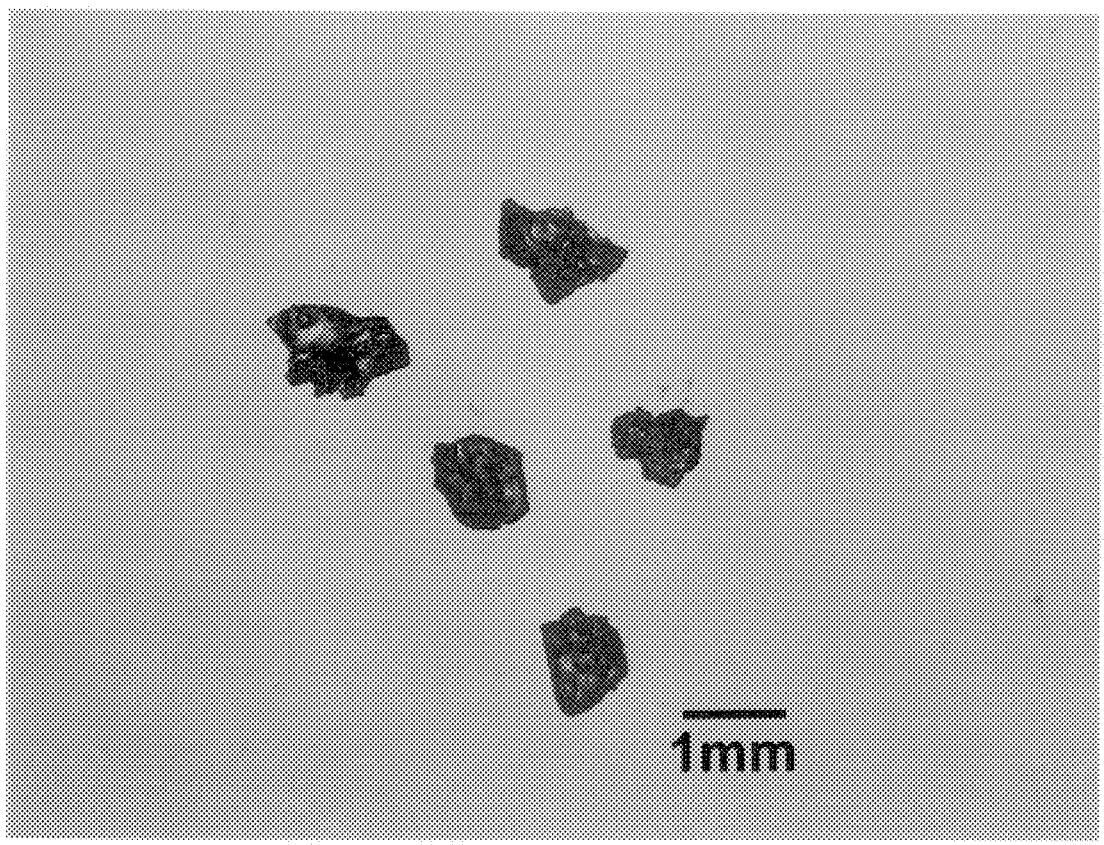
FIG. 8A representatively shows magnified a top view of a quantity of relatively dry superabsorbent material after conditioning at approximately 80% relative humidity and 100° F. and prior to compressing under a low force.
Figure 8B:
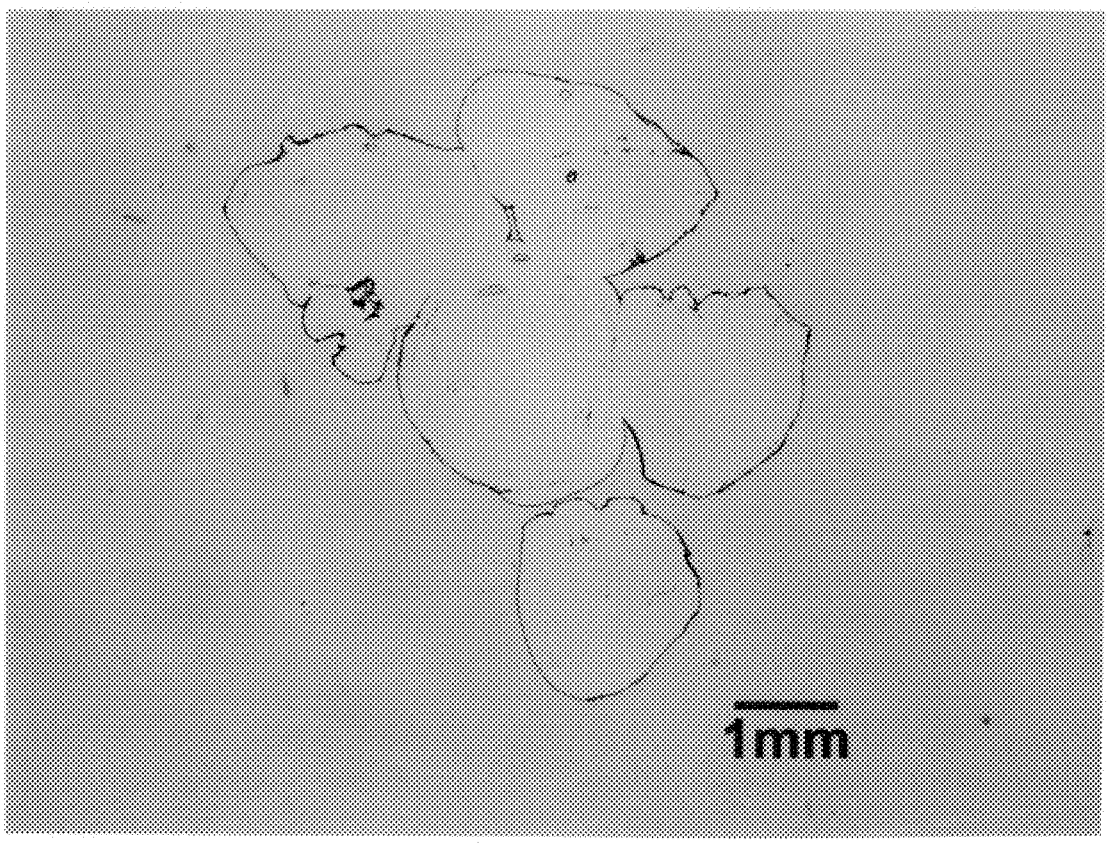
FIG. 8B representatively shows a magnified top view of the superabsorbent material of FIG. 8A during compression.
Figure 8C:
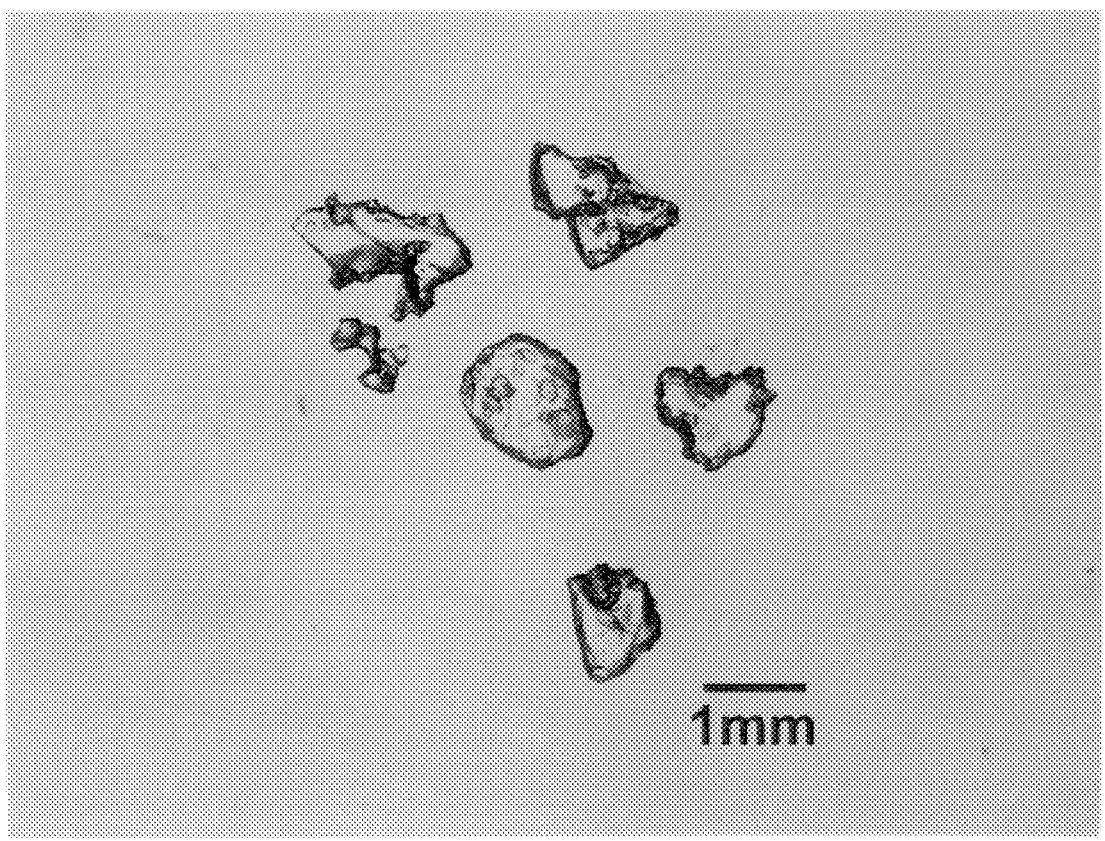
FIG. 8C representatively shows a magnified top view of the superabsorbent material of FIG. 8B, as observed immediately after the superabsorbent has been compressed and the compressing pressure has been released, wherein the compressed superabsorbent material has recovered from its deformed condition and is substantially unfractured.
Figure 8D:
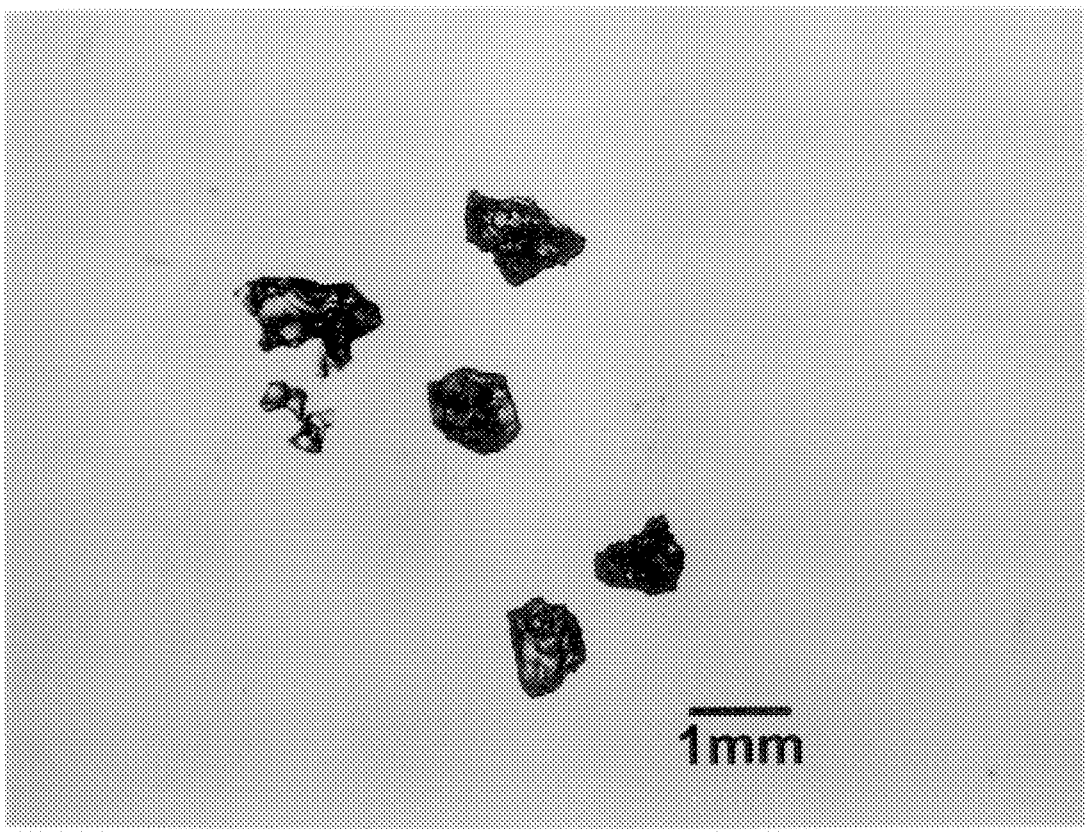
FIG. 8D representatively shows a magnified top view of the superabsorbent material of FIG. 8C, as observed approximately 5 minutes after the compressing pressure has been released, wherein the compressed superabsorbent material has further recovered from its deformed shape and is substantially unfractured.

A third sample (Example 23) was composed of particles of superabsorbent material which had been conditioned in a 80% RH and a 100° F. (38° C.) environment for 24 hours. FIG. 8 shows the dry superabsorbent, and FIG. 8A shows that, after conditioning, the superabsorbent particles have enlarged slightly. The sample was placed between a pair of glass microscope slides and the slides were pressed together with a mild, finger-applied force. FIG. 8B shows the deformation of the superabsorbent particles during compression, and FIG. 8C shows that, after compression, the superabsorbent particles in this sample had immediately rebounded when the compressing force was released. FIG. 8D shows that, approximately 5 minutes after the compressing force was released, the superabsorbent particles in this sample had rebounded to substantially their original size and shape.

EXAMPLES 24–25

Figure 9:
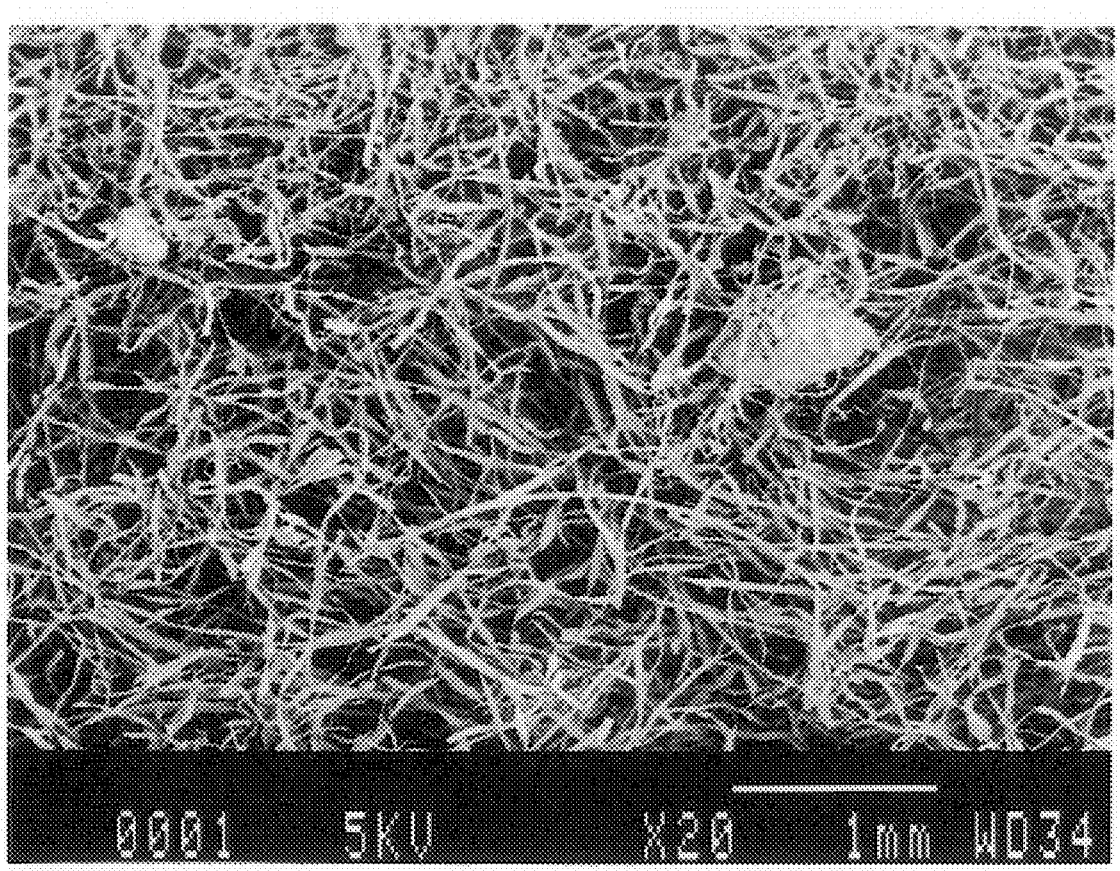
FIG. 9 is a scanning electron microscope (SEM) photomicrograph which representatively shows a cross-sectional view of a composite composed of superabsorbent particles in a fiber matrix prior to compressing.
Figure 9A:
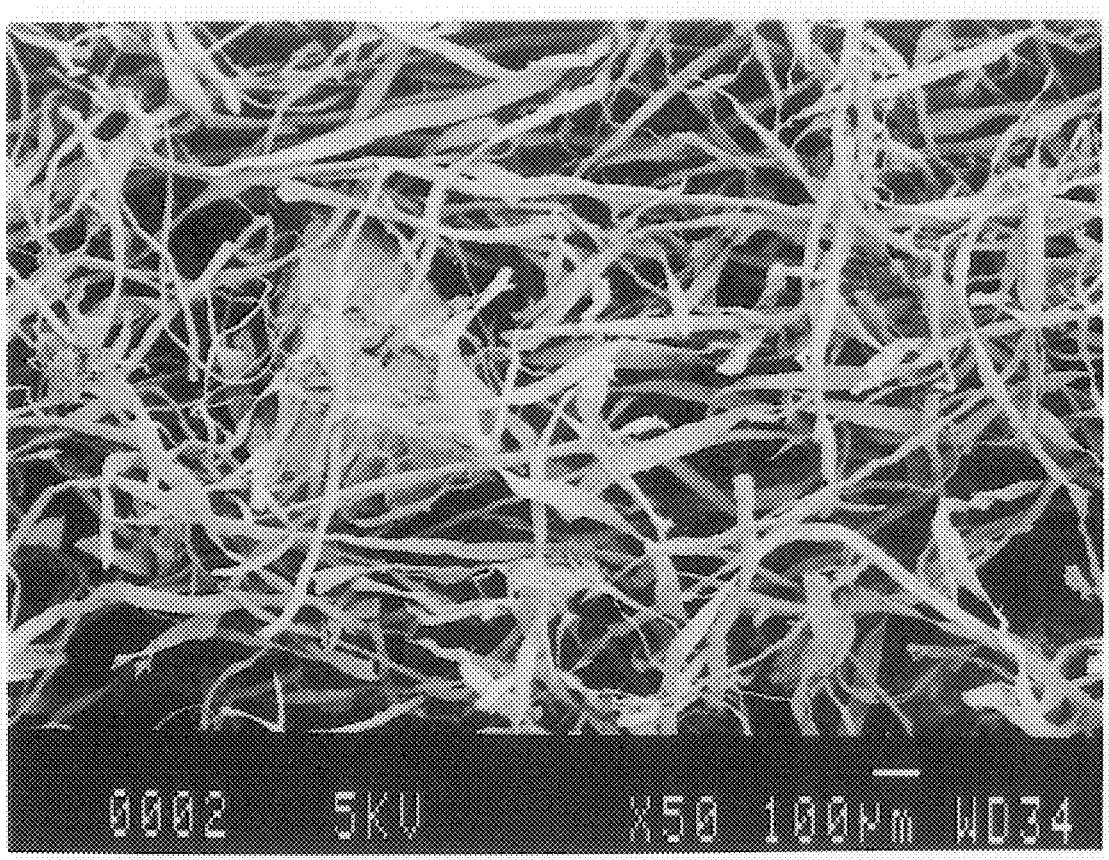
FIG. 9A is a scanning electron microscope (SEM) photomicrograph which representatively shows a further enlarged, cross-sectional view of a portion of the composite of FIG. 9.

Two composite samples were composed of superabsorbent particles and wood pulp fluff, and were constructed employing FAVOR 880 superabsorbent. The samples were constructed in accordance with the description in Example 20. The first composite sample (Example 24) was conditioned at a relative humidity of less than 20% and a temperature of 130° F. (54° C.) to provide a 0.65 wt % moisture level in the composite. The other composite sample (Example 25) was conditioned in a high humidity environment of 80% RH and 100° F. (38° C.) temperature prior to compression to provide a moisture level of 35.3 wt % in the composite. The typical structure and condition of a composite sample prior to compressing and compacting are representatively shown in FIGS. 9 and 9A. The samples of Examples 24 and 25 were highly compressed by passing each sample through a 0.012 inch (0.3 mm) gap between a pair of cylindrical, metal compression rollers. The composite samples measured 4 inch (10.2 cm) in their cross-directional width (along the axial dimension of the compression rollers), and were passed through the compression gap at a speed of 113 ft/min (34 m/min).

Figure 10:
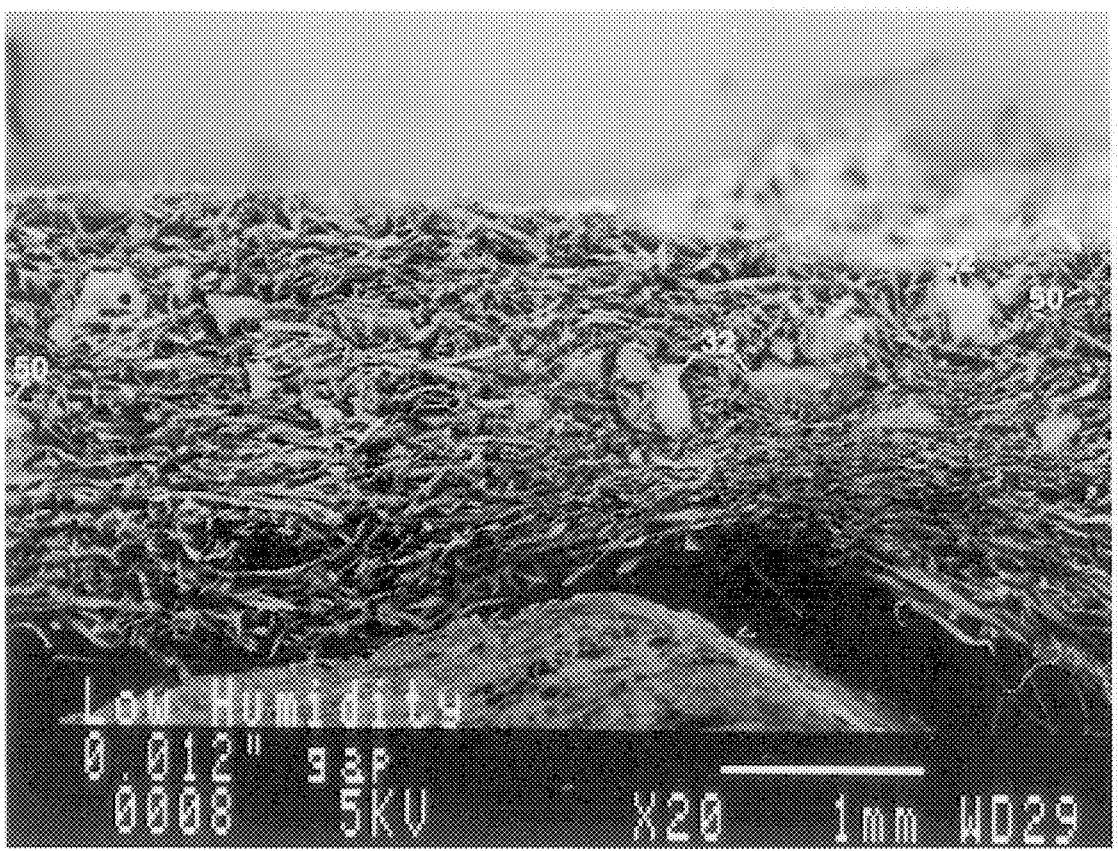
FIG. 10 is a SEM photomicrograph which representatively shows a cross-sectional view of a composite composed of relatively dry superabsorbent particles in a fiber matrix, as observed after the composite was compressed.
Figure 10A:
FIG. 10A is a SEM photomicrograph which representatively shows a cross-sectional view of a portion of the composite of FIG. 10 at an enlarged, higher magnification.
Figure 10B:
FIG. 10B is a SEM photomicrograph which representatively shows an enlarged, cross-sectional view of another portion of the composite of FIG. 10.

FIGS. 10 through 10B representatively show the fibers 50 and superabsorbent particles 32 in the compressed composite of Example 24, which contained the relatively dry superabsorbent. When the superabsorbent particles are contained in the woodpulp fluff matrix, the fluff fibers can have a cushioning effect when the structure is compressed, as evidenced by observing how the fibers have been molded around the particles. Consequently, some particles can survive without fracturing, but many of the particles are fractured, e.g. cracked or broken.

Figure 11:
FIG. 11 is a SEM photomicrograph which representatively shows a cross-sectional view of a composite composed of relatively high-moisture-content superabsorbent particles in a fiber matrix, as observed after the composite was compressed.
Figure 11A:
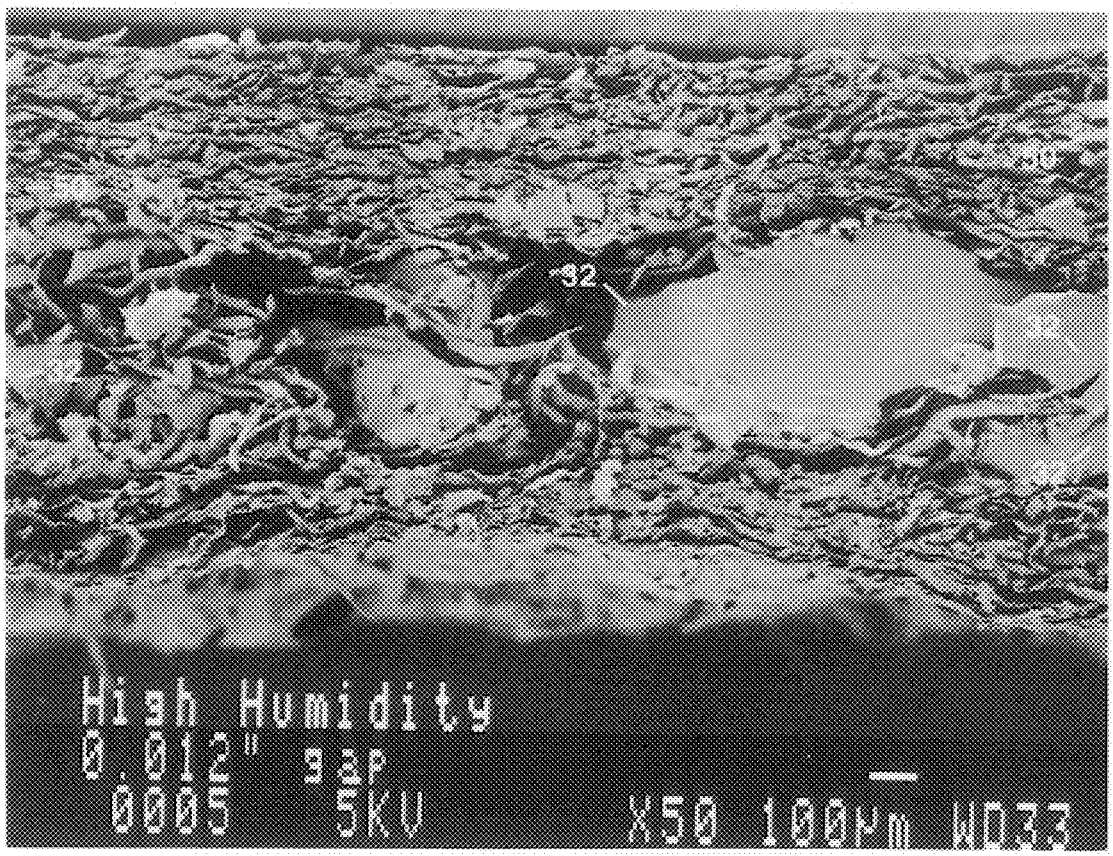
FIG. 11A is a SEM photomicrograph which representatively shows a cross-sectional view of a portion of the composite of FIG. 11 at an enlarged, higher magnification.
Figure 11B:
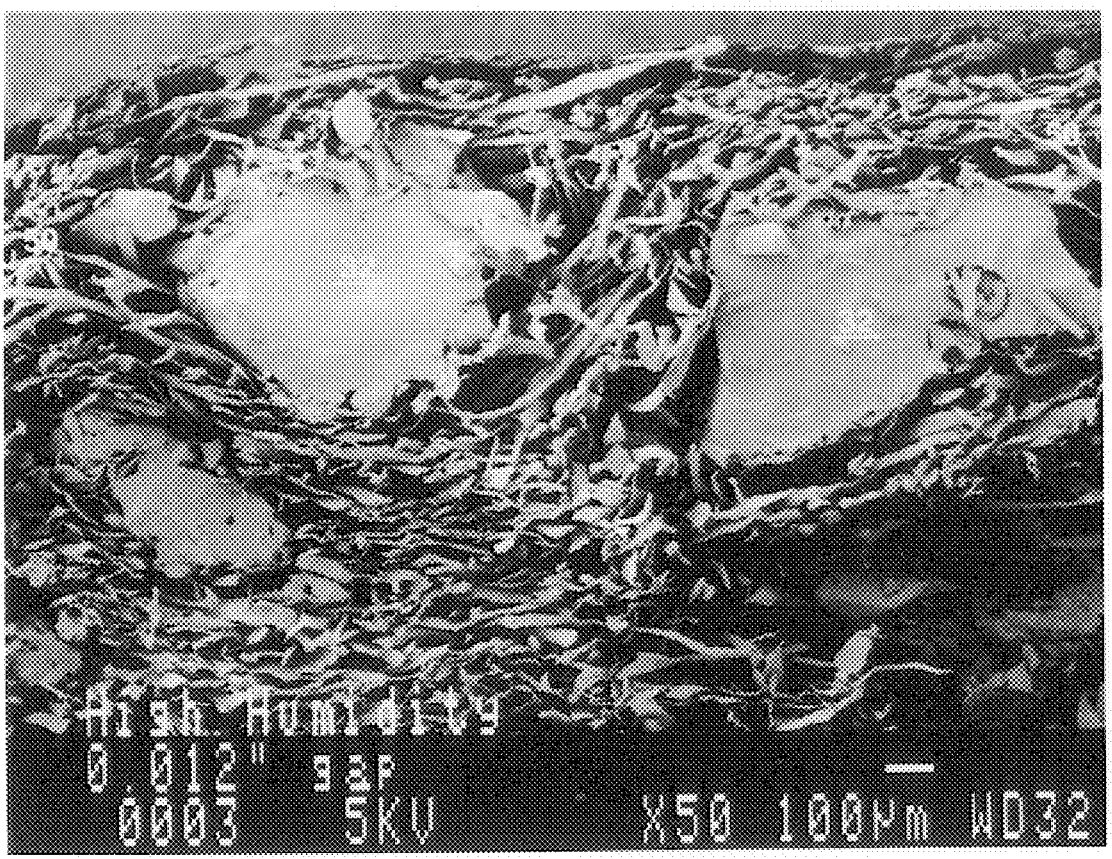
FIG. 11B is a SEM photomicrograph which representatively shows an enlarged, cross-sectional view of another portion of the composite of FIG. 11.
Figure 11C:
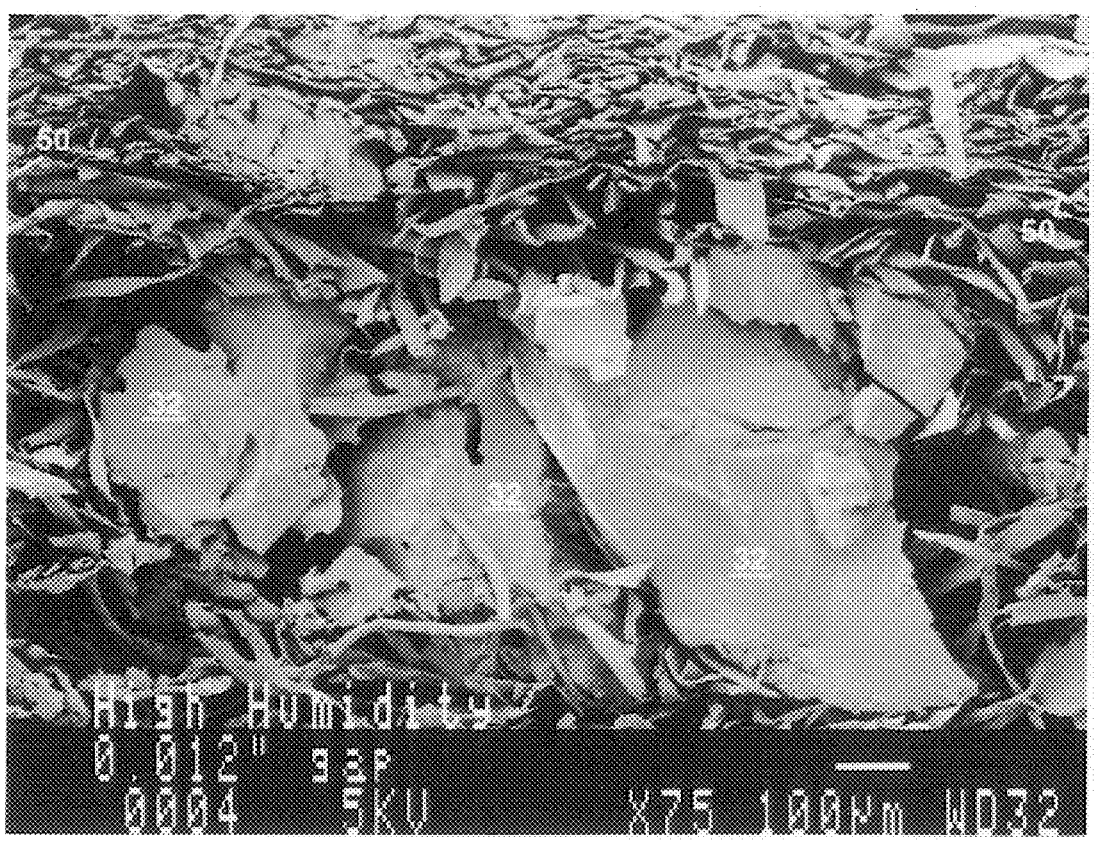
FIG. 11C is a SEM photomicrograph which representatively shows an enlarged, cross-sectional view of yet another portion of the composite of FIG. 11.

FIGS. 11 through 11C representatively show the fibers 50 and superabsorbent particles 32 in the compressed composite of Example 25, which contained the humidified, high-moisture-content superabsorbent. The humidified superabsorbent particles became rubbery, and deformed greatly without breaking. Additionally, the superabsorbent particles rebounded to substantially their original size and shape once the compressing forces were released. The rebounding force of the particles was evidently great enough to spread the compacted fluff fibers apart, e.g. in the z-direction. The combined effect of the lateral spreading of the superabsorbent particles under compression and the z-direction expansion of the matrix as the superabsorbent particles regained their shape advantageously generated spaces in the fluff matrix in the regions that are immediately adjacent to the particles (e.g. FIG. 11). Consequently, the fibers above and below the particles remained very compressed, and the fluff laterally between particles was relatively less compressed.

Moisture Content of Superabsorbent

For the purposes of the present disclosure the moisture content of superabsorbent can be determined by drying a 5 gram sample of the "wet" superabsorbent in an oven at 105° C. for 3 hours. The percent moisture can be calculated by employing the following formula:

$$\text{Percent Moisture} = 100 * (Wt_{wet} - Wt_{dry})/Wt_{wet}$$

Moisture Content of Composites

For the purposes of the present disclosure the moisture content of the superabsorbent and fluff composite was determined by drying a sample of the "wet" composite in an oven at 105° C. for 18 hours. The percent moisture can be calculated by employing the following formula:

$$\text{Percent Moisture} = 100 * (Wt_{wet} - Wt_{dry})/Wt_{wet}$$

Absorbency Under Load

A suitable technique for determining the Absorbency Under Load at a pressure of 0.9 psi (6.2 KPa) is described in detail in U.S. Pat. No. 5,601,542 entitled ABSORBENT COMPOSITE by M. K. Melius et al. granted Feb. 11, 1997, the entire disclosure of which is hereby incorporated by reference in a manner that is consistent herewith. For the purposes of the present disclosure, a 400 mesh stainless steel wire cloth was substituted for the 100 mesh wire cloth adhered on the bottom of the AUL-test cylinder cup. The 400 mesh screen was employed to better contain the particles that might have been crushed and fallen through the 100 mesh screen. In addition, only the 0.9 psi AUL needs to be determined.

In accordance with the above-described AUL procedure, the amount (in grams) of liquid picked up after 60 minutes, divided by the weight of the sample (0.160 gram) is the AUL value in grams of liquid picked up per gram of sample (g/g). On a dry weight basis, the moisture level of the superabsorbent was measured independently and the weight of the superabsorbent in the denominator was adjusted accordingly: the amount of liquid picked up after 60 minutes, divided by the dry weight of the sample (0.160–0.160 * moisture in %/100) is the dry weight basis AUL value.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. A process for compacting a web which contains a superabsorbent material, said process comprising a moving of said web; and a compressing of the moving web; wherein said web has been provided with at least about 5 wt % of superabsorbent material, and said superabsorbent material has been plasticized.

2. A process for compacting a web which contains a superabsorbent material, said process comprising:
   a plasticizing of said superabsorbent material contained in said web;
   a moving of said web along a machine-direction;
   a compressing of the moving web; and
   a providing of said web with at least about 5 wt % of superabsorbent material.

3. A process as recited in claim 1, wherein said compressing is provided at a pressure which substantially avoids fracturing said superabsorbent material.

4. A process as recited in claim 1, wherein said process provides said web with a density of at least about 0.2 g/cm$^3$.

5. A process as recited in claim 1, wherein said compressing of said web subjects said web to a compressing gap which is less than about 2 mm.

6. A process as recited in claim 1, wherein said compressing of said web subjects said web to a compressing gap which is less than about 1 mm.

7. A process as recited in claim 1, wherein said compressing of said web subjects said web to a compressing gap which is less than a median particle size of said superabsorbent material.

8. A process as recited in claim 1, wherein
   said web has been initially provided while said superabsorbent material contains a first moisture level; and
   said process further includes a conducting of said compressing of said web while said superabsorbent material contains a second moisture level which is greater than said first moisture level.

9. A process as recited in claim 1, further comprising a providing of fibrous material for inclusion in said web.

10. A process as recited in claim 1, further comprising a flexing of said web.

11. A process as recited in claim 10, wherein said flexing of said web is conducted prior to said compressing of said web.

12. A process as recited in claim 11, wherein said flexing of said web includes a cross-directional flexing of said web.

13. A process as recited in claim 12, wherein said cross-directional flexing of said web includes a passing of said web through a nip between a pair of cooperating, circumferentially-grooved rollers.

14. A process as recited in claim 11, wherein said flexing of said web includes a machine-directional flexing of said web.

15. A process as recited in claim 14, wherein said machine-directional flexing of said web includes a moving of said web along a curved path which curves through a turning angle of at least about 15 degrees.

16. A process as recited in claim 14, wherein said machine-directional flexing of said web includes a moving of said web along a curved path which curves through a turning angle of at least about 15 degrees and has a radius of curvature within the range of about 1–20 cm.

17. A process as recited in claim 14, wherein said machine-directional flexing of said web includes a moving of said web along a substantially S-shaped curved path which curves through a cumulative, reflexed turning angle of at least about 180 degrees.

18. A process as recited in claim 1, wherein said plasticizing of said superabsorbent material includes a humidifying of said web.

19. A process as recited in claim 18, wherein said humidifying of said web includes an exposing of said web to a relative humidity of not more than about 100% at a temperature of not more than about 100° C.

20. A process as recited in claim 18, wherein said humidifying of said web includes an exposing of said web to a relative humidity of at least about 80% at a temperature of at least about 20° C.

21. A process as recited in claim 1, wherein said compressing of said web includes a passing of said web through a nip between a pair of cooperating, counter-rotating, circumferentially-grooved rollers.

22. A process as recited in claim 1, further comprising a heating of said web.

23. A process as recited in claim 22, wherein said heating of said web is conducted concurrently with said compressing of said web.

24. A process as recited in claim 22, wherein said heating of said web is conducted substantially simultaneously with said compressing of said web.

25. A process as recited in claim 22, wherein said web is passed through a nip between a pair of counter-rotating, heated calendering rollers.

26. A process as recited in claim 22, wherein said heating of said web subjects said web to a temperature of at least about 20° C.

27. A process as recited in claim 26, wherein said heating of said web subjects said web to a temperature of not more than about 205° C.

28. A process as recited in claim 22, wherein said heating of said web includes a subjecting of said web to a temperature of at least about 80% of a glass transition temperature of said superabsorbent material.

29. A process as recited in claims 28, wherein said heating of said web includes a subjecting of said web to a temperature of not more than about 125% of the glass transition temperature of said superabsorbent material.

30. A process as recited in claim 1, wherein said web has been provided with a content of at least about 10 wt % of fibrous material.

31. A process as recited in claim 30, wherein said web has been provided with a content of not more than about 90 wt % of superabsorbent material.

32. A process as recited in claim 1, wherein said web has been wet-formed by employing a mixture of said superabsorbent material and a fibrous material.

33. A process as recited in claim 32, wherein said web has been wet-formed by employing a water-containing mixture of said superabsorbent material and said fibrous material.

34. A process as recited in claim 32, wherein said mixture of said superabsorbent material and said fibrous material has been provided in the configuration of a foam.

35. A process as recited in claim 1, wherein said web has been dry-formed by employing a mixture of said superabsorbent material and a fibrous material.

36. A process as recited in claim 35, wherein said web has been dry-formed by employing an air-suspension of said superabsorbent material and said fibrous material.

37. A process as recited in claim 1, wherein said superabsorbent has a composition which has been chemically adjusted to provide a glass transition temperature of less than about 35° C. at a relative humidity of 50%.

38. A process for compacting a web which contains a superabsorbent material, said process comprising a compressing of said web; wherein
    said superabsorbent material has been plasticized,
    said compressing of said web subjects said web to a compressing gap which is less than about 2 mm, and
    said web has been provided with at least about 5 wt % of superabsorbent material.

39. A process for compacting a web which contains a superabsorbent material, said process comprising a compressing of said web, and a flexing of said web; said superabsorbent material having been plasticized, and said web having been provided with at least about 5 wt % of superabsorbent material.

40. A process as recited in claim 39, wherein said flexing of said web is conducted prior to said compressing of said web.

41. A process for compacting a web which contains a superabsorbent material, said process comprising a compressing of said web with counter-rotating rollers; wherein said superabsorbent material has been plasticized, and said web has been provided with at least about 5 wt % of superabsorbent material.

42. A process as recited in claim 41, further including a cross-directional flexing of said web.

43. A process as recited in claim 42, further including a machine-directional flexing of said web.

* * * * *

UNITED STATES PATENT AND TRADEMARK OFFICE
CERTIFICATE OF CORRECTION

PATENT NO.    : 6,214,274 B1
DATED         : April 10, 2001
INVENTOR(S)   : Shannon Kathleen Melius, et al.

Page 1 of 1

It is certified that error appears in the above-identified patent and that said Letters Patent is hereby corrected as shown below:

Title page,
Item [22], Filed: June 16, 1999, insert heading -- Related U.S. Application Data --, then also insert -- [60] Provisional application No. 60/134,361, filed May 14, 1999 --.

Column 5,
Line 34, delete "grasslike", and substitute -- glasslike --.
Line 50, delete "*Encycloredia*", and substitute -- *Encyclopedia* --.

Column 15,
Line 35, delete "desk".

Column 19,
Line 3, delete "*Parerboard*", and substitute -- *Paperboard* --.

Column 23,
Last row of Table 5, delete "1778", and substitute -- 1.778 --.

Signed and Sealed this

Twelfth Day of March, 2002

*Attest:*

*Attesting Officer*

JAMES E. ROGAN
*Director of the United States Patent and Trademark Office*